(12) United States Patent
Reed

(10) Patent No.: US 12,207,975 B2
(45) Date of Patent: Jan. 28, 2025

(54) PORTABLE DEVICE AND METHOD OF SUPPLYING POWER TO A PORTABLE DEVICE

(71) Applicant: PELETON SURGICAL, LLC, Scottsdale, AZ (US)

(72) Inventor: David John Reed, Sheffield (GB)

(73) Assignee: PELETON SURGICAL, LLC, Scottsdale, AZ (US)

( * ) Notice: Subject to any disclaimer, the term of this patent is extended or adjusted under 35 U.S.C. 154(b) by 573 days.

(21) Appl. No.: 17/532,170

(22) Filed: Nov. 22, 2021

(65) Prior Publication Data

US 2022/0079702 A1 Mar. 17, 2022

Related U.S. Application Data

(63) Continuation-in-part of application No. 16/915,228, filed on Jun. 29, 2020, now Pat. No. 11,183,855, which is a continuation-in-part of application No. 15/830,347, filed on Dec. 4, 2017, now Pat. No. 10,700,538, which is a continuation-in-part of application No. 14/987,428, filed on Jan. 4, 2016, now Pat. No. 9,837,839.

(51) Int. Cl.
*A61B 90/00* (2016.01)
*A61B 50/33* (2016.01)
*G06F 1/26* (2006.01)

(52) U.S. Cl.
CPC .............. *A61B 90/08* (2016.02); *A61B 50/33* (2016.02); *G06F 1/263* (2013.01); *A61B 2090/0813* (2016.02)

(58) Field of Classification Search
CPC . A61B 90/08; A61B 50/33; A61B 2090/0813; G06F 1/263
USPC ........................................................ 320/137
See application file for complete search history.

(56) References Cited

U.S. PATENT DOCUMENTS

2012/0110824 A1* 5/2012 Smith .................... H02J 7/0044
                                                                29/271
2012/0112690 A1* 5/2012 Stulen ....................... H02J 7/02
                                                                320/108

* cited by examiner

*Primary Examiner* — Nathaniel R Pelton
(74) *Attorney, Agent, or Firm* — POLSINELLI PC

(57) ABSTRACT

A portable device and method of supplying power to the portable device may provide a sterile environment that may protect the health and safety of patients on whom the device is employed. The portable device may be charged inside of the sterile environment. The portable device may be charged using at least one chargeable battery that may be arranged internal and/or external to a portion of the portable device, or internal and/or external to the portable device. A power supply may be connected to the at least one chargeable battery and power the portable device for use. The portable device may be charged up to 100% and/or or fully charged prior to opening the sterile environment.

12 Claims, 22 Drawing Sheets

PORTABLE DEVICE AND METHOD OF SUPPLYING POWER TO A PORTABLE DEVICE

CROSS REFERENCE TO RELATED APPLICATION

This application is a continuation-in-part application of U.S. application Ser. No. 16/915,228, filed Jun. 29, 2020, which is a continuation-in-part application of U.S. application Ser. No. 15/830,347, filed Dec. 4, 2017, which is a continuation-in-part application of U.S. application Ser. No. 14/987,428, filed Jan. 4, 2016, now U.S. Pat. No. 9,837,839, the entire contents of each is incorporated herein by reference.

FIELD OF THE INVENTION

The present disclosure generally relates to a power tool and a method of supplying power to a power tool, and more particularly to a portable device powered by a chargeable battery and a method of supplying power to the portable device powered by a chargeable battery.

BACKGROUND

Medical equipment and instruments are required to maintain an aseptic condition in order to protect the safety and health of patients. With the advancement of science and technology, using electrical medical equipment has become more common. However, one problem associated with using electrical medical equipment includes difficulty with safely transporting equipment over long-distances, thereby compromising the safety and health of patients that require electrical medical equipment. Additionally, prior to being shipped, medical equipment and instruments are typically only charged between 10% and 50% of their full capacity. As such, in order to ensure medical operations are safely performed, medical equipment and instruments must be charged and require a sterile power supply. In the event of an unexpected or tragic incident, e.g., an earthquake, typhoon, blizzard, or widespread power outage, charging medical equipment may not be possible. Further, geographic locations that do not have access to an adequate power supply and/or sterile environment cannot fully charge medical equipment and instruments.

While mobile power supplies are available, existing power supply devices and methods of supplying power are not able to charge medical equipment and instruments located in a sealed and sterile environment. Rather, these power supplies and methods thereof are surrounded by dust and bacteria, and are susceptible to contact by harmful fluids. Accordingly, the sterility and safety of using these power supplies to charge electrical medical equipment and instruments is degraded and the service life is significantly reduced. Additionally, the patient's health can be compromised.

SUMMARY

Embodiments of the present disclosure may provide a method for supplying power to a portable device that may be powered by at least one chargeable battery. The method may provide sealing the portable device in a sterile environment using a first microbial barrier, and the first microbial barrier may maintain the sterile environment. The method may provide charging the portable device in the sterile environment. A power supply may be arranged to supply power to the at least one chargeable battery contained in the portable device. The method may provide sealing the portable device in the sterile environment using a second microbial barrier. The second microbial barrier may provide protection in addition to the first microbial barrier to maintain the sterile environment. The method may provide arranging the at least one chargeable battery inside of a portion of the portable device, arranging the at least one chargeable battery external to the portion of the portable device, and/or arranging the at least one chargeable battery external to the portable device. The method may provide charging the portion of the portable device to a full capacity prior to opening the sterile environment.

Embodiments of the present disclosure may provide a portable device that may be powered by at least one chargeable battery. The portable device may provide at least one microbial barrier that may be arranged to seal the portable device, and the at least one microbial barrier may maintain a sterile environment for the portable device. The portable device may provide a portion of the portable device that may include a charging port, a first tray that may be configured to receive and secure the portion of the portable device, a second tray that may be configured to receive and secure the first tray, a package that may be configured to receive the second tray, and at least one chargeable battery. The at least one chargeable battery may be configured to power the portable device. At least one cable may connect the at least one chargeable battery to the charging port, and a power supply may be arranged to supply power to the at least one chargeable battery. The at least one chargeable battery may be arranged inside of the portion of the portable device, may be arranged external to the portion of the portable device, and/or may be arranged external to the portable device. The portable device may be charged to a full capacity prior to opening the sterile environment.

A system for supplying power to a portable device may be provided in a sterile environment. The system may provide securing a portion of the portable device in a first tray, and the portion of the portable device may include a charging port for receiving power. The system may provide covering the first tray with a first microbial barrier and connecting the portion of the portable device to the first tray using a first connecting cable. The system may provide securing the first tray in a second tray and covering the second tray with a second microbial barrier. Further, the system may provide connecting the first tray and the second tray using a second connecting cable and connecting the second tray to a package using a third connecting cable. The system may provide securing the second tray in the package and supplying power to the portable device using at least one chargeable battery. The at least one chargeable battery may be arranged inside of the portion of the portable device, may be arranged external to the portion of the portable device, and/or may be arranged external to the portable device. The portable device may be charged to a full capacity prior to opening the sterile environment.

A method for supplying power to a portable device may be provided. The method may provide for sealing the portable device in a sterile environment using a first tray, a first microbial barrier, a second tray, and a second microbial barrier. The first tray may be configured to receive and secure the portable device, wherein the first microbial barrier is arranged to seal the first tray and maintain a sterile environment for the portable device. The second tray may be configured to receive and secure the first tray in the second tray, wherein the second microbial barrier is arranged to seal the second tray and maintain a sterile environment for the portable device. The method may further provide for charging the portable device in the sterile environment, wherein a power supply supplies power to at least one chargeable battery contained in the portable device. The power supply may supply power via a wireless charging station located external to the portable device. The power supply may have a transmitter operable to transmit power wirelessly to a receiver secured in the portable device. The at least one chargeable battery is operable to power the portable device.

The method may further provide inducing a magnetic field using the transmitter, wherein the transmitter is a transmitter coil operable to induce a magnetic field using an AC current. The method may further provide securing the receiver in a portion of the portable device, wherein the receiver is a receiver coil operable to receive the AC current. The method may further provide converting the AC current to a DC current via the receiver coil. The method may further provide delivering the DC current to the at least one chargeable battery via a first relay cable secured within the second tray and a second relay cable secured within the first tray, wherein the second relay cable is connected to the charging port at a first end and connected to the first relay cable at a second end opposite the first end and the first relay cable is connected to the receiver. The method may further provide maintaining the at least one chargeable battery via a charging system comprising a chip or a PCB operable to control a charge current to the at least one chargeable battery. The method may further provide disconnecting the at least one chargeable battery from the power supply via a fuse when a fuse triggering event occurs. The fuse triggering event may occur when the at least one chargeable battery receives a power greater than a power threshold. The fuse may be resettable and reusable. The method may further provide authorizing a user to reset the fuse using a trigger operable to prevent fuse resetting without an authorization.

A system for supplying power to a portable device provided in a sterile environment may be provided. The system may provide securing a portion of the portable device in a first tray, wherein the portion of the portable device includes a wireless receiver for receiving power. The system may provide covering the first tray with a first microbial barrier. The system may provide securing the first tray in a second tray. The system may provide covering the second tray with a second microbial barrier. The system may provide connecting the second tray to a package using a third connecting cable. The system may provide securing the second tray in the package. The system may provide supplying power to the portable device using at least one chargeable battery via a wireless charging station having a transmitter operable to transmit power wirelessly to the receiver. The transmitter may be a transmitter coil operable to induce a magnetic field using an AC current. The wireless receiver may be a receiver coil secured in the second tray and operable to receive the AC current. The receiver coil may be operable to convert the AC current to a DC current.

The system may further provide a first relay cable secured within the second tray and a second relay cable secured within the first tray, wherein the second relay cable is connected to the charging port at a first end and connected to the first relay cable at a second end opposite the first end the first relay cable is connected to the receiver coil. The system may further provide a charging system operable to maintain the at least one chargeable battery, the charging system comprising a chip or a PCB operable to control a charge current to the at least one chargeable battery. The system may further provide further comprising a fuse operable to disconnect the at least one chargeable battery from the power supply when a fuse triggering event occurs. The fuse triggering event may occur when the at least one chargeable battery receives power greater than a power threshold. The fuse may be resettable and reusable. The system may further provide a trigger operable to prevent fuse resetting without an authorization.

A system may further provide a plurality of portable devices, a first tray, a first microbial barrier, a second tray, a second microbial barrier, a package, and a power supply. Each of the portable devices may be powered by at least one chargeable battery. The first tray may be operable to receive and secure the plurality of portable devices. The first microbial barrier may be arranged to seal the first tray and maintain a sterile environment for the portable devices. The second tray may be operable to receive and secure the first tray in the second tray. The second microbial barrier may be arranged to seal the second tray and maintain a sterile environment for the portable devices. The package may be operable to receive the second tray and provide a sterile enclosure for the plurality of portable devices. The power supply may be operable to be electrically connected with each of the plurality of portable devices such that the chargeable batteries of each of the portable devices may be charged in the sterile environment.

The chargeable batteries may be arranged inside of the portable devices. The chargeable batteries may be arranged external to the portable devices and contained within the first tray. Each of the portable devices may be charged to a full capacity prior to opening the sterile environment. The power supply may supply power to each of the chargeable batteries corresponding with the portable devices via a wireless charging station located external to the portable devices having a transmitter operable to transmit power wirelessly to a receiver secured in each of the portable devices. The power supply may supply power to each of the chargeable batteries corresponding with the portable devices via wired connection. The system may further provide a plurality of first connecting cables and a plurality of second connecting cables electrically connected to corresponding first connecting cables. The first connecting cables may be secured within the first tray and the second connecting cables may be secured within the first tray and the second tray. The power supply may be electrically connected with the second connecting cable to supply power to each of the chargeable batteries corresponding with the portable devices. A charging system may be included to maintain the chargeable batteries. The charging system may include a chip or a PCB operable to control a charge current to the chargeable batteries. A fuse may be included and operable to disconnect the chargeable batteries from the power supply when a fuse triggering event occurs.

Other technical features may be readily apparent to one skilled in the art from the following figures, descriptions and claims.

BRIEF DESCRIPTION OF THE DRAWINGS

For a more complete understanding of this disclosure, reference is now made to the following description, taken in conjunction with the accompanying drawings, in which.

DETAILED DESCRIPTION

Figure 1:
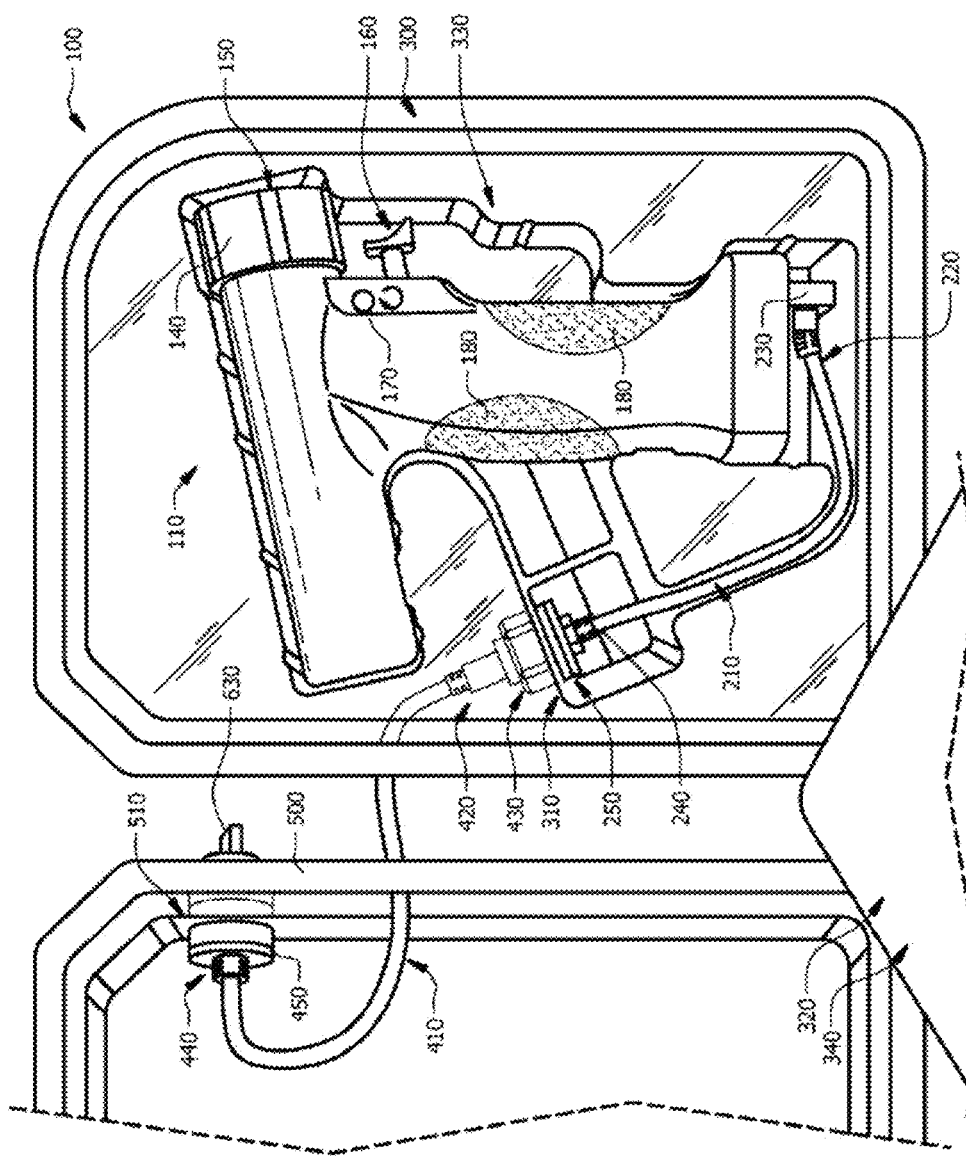
FIG. 1 depicts a portable device according to an embodiment of the present disclosure.

As shown in FIG. 1 according to an embodiment of the present disclosure, portable device that may be powered by at least one chargeable battery (hereinafter, "portable device") 100 may include portion 110 of portable device 100 that may be charged to a full capacity in a sterile environment and may be sealed by at least first microbial barrier 340. It should be appreciated that portable device 100 may be powered by a plurality of energy sources including, but not limited to, batteries and/or capacitors. Portion 110 may be secured within compartment 330 of first tray 300. Compartment 330 may be molded to the shape of portion 110 and the shape of first connecting cable 210, thereby securing portion 110 and first connecting cable 210 within first tray 300. It should be appreciated that portion 110 of portable device 100 may be a handpiece, a handle, or a gripping mechanism according to embodiments of the present disclosure. First tray 300 may be covered and sealed using first breathable lid or cover 320 and may be made from a material that may include first microbial barrier 340. First breathable lid or cover 320 may include first microbial barrier 340 to maintain a sterile environment for portable device 100. It should be appreciated that first microbial barrier 340 may provide sterile asepsis to eliminate micro-organisms from portable device 100. It should be appreciated that first tray 300 may be a blister pack that may be made of plastic or other similar material without departing from the present disclosure. It should be appreciated that first tray 300, second tray 500, and package 700 (FIG. 3 and FIG. 5) may prevent portable device 100 from sustaining damage during shipment. First connector 230 may include a male connector and may be provided at first end 220 of first connecting cable 210. It should be appreciated that a male connector may be a universal serial bus (USB), a male cord end, and/or male wire end without departing from the present disclosure. Second connector 250 of first connecting cable 210 may be provided at second end 240 opposite first end 220, and second end 240 may be secured within first wall 310 of first tray 300. Second connector 250 may include a female port that may be provided to receive third connector 430 of second connecting cable 410. It should be appreciated that a female port may include, but is not limited to, a USB port, a female cord end, and/or female wire end without departing from the present disclosure.

Figure 3:
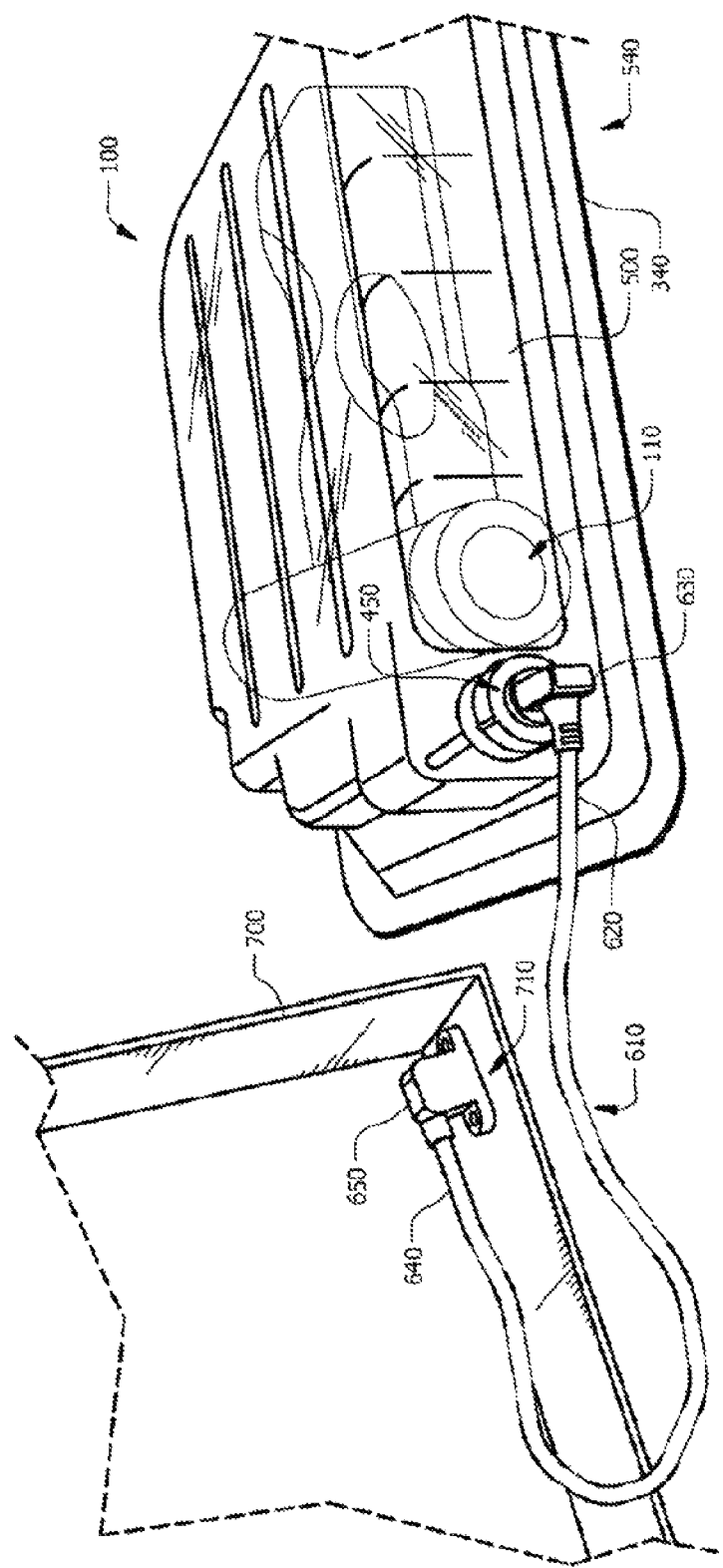
FIG. 3 depicts a perspective view of a portable device including microbial barriers and a package according to an embodiment of the present disclosure.

As shown in FIG. 1 according to an embodiment of the present disclosure, second connecting cable 410 may provide third connector 430, and third connector 430 may be provided at third end 420 of second connecting cable 410. Third connector 430 may include a male connector. Fourth connector 450 of second connecting cable 410 may include a female port that may be provided to receive fifth connector 630 of third connecting cable 610 (FIG. 3). It should be appreciated that first connecting cable 210 may be removed from within first wall 310 by disconnecting third connector 430 from second connector 250. Fourth connector 450 may be provided at fourth end 440 of second connecting cable 410 opposite third end 420. It should further be appreciated that second connecting cable 410 may be removed from within second wall 510 of second tray 500 by disconnecting fifth connector 630 from fourth connector 450. It should be appreciated that each connecting cable may be removed from a connection with a wall, package, or another connecting cable by unscrewing or disengaging each male-female connection. Second tray 500 may be covered and sealed using second breathable lid or cover 520 (FIG. 3) that may be made from a material that may include second microbial barrier 540 in some embodiments of the present disclosure. Second breathable lid or cover 520 may include second microbial barrier 540 to maintain a sterile environment for portable device 100. It should be appreciated that second microbial barrier 540 may provide sterile asepsis to eliminate micro-organisms from the portable device. It should be appreciated that cover 320 and cover 520 may provide a double layer of protective microbial barriers 340, 540 that may help to protect the sterility of portable device 100. It should be appreciated that a plurality of microbial barriers may be provided to create a sterile environment without departing from the present disclosure. It should further be appreciated that cover 320 and cover 520 may form a primary packaging for portable device 100 without departing from the present disclosure.

As shown in FIG. 1 according to an embodiment of the present disclosure, second wall 510 of second tray 500 may house a connection between fourth connector 450 and fifth connector 630. Fourth connector 450 may receive fifth connector 630. Fifth connector 630 may include a male connector. Sixth connector 650 may include a female port that may be accessible from an exterior of package 700 (FIG. 3) using sixth connector 650. It should be appreciated that a male connector may include, but is not limited to, a male USB connector, a male cord end, and/or male wire end and a female port may include, but is not limited to, a female USB port, a female cord end, and/or female wire end without departing from the present disclosure. Portable device 100 may be charged while inside of package 700, first tray 300, and second tray 500 by connecting power supply 800 (FIG. 4) to sixth connector 650 in embodiments of the present disclosure.

It should be appreciated that package 700, first tray 300 and second tray 500 may create a sterile barrier system (SBS). It should be appreciated that the SBS may prevent an ingress of microorganisms from reaching portable device 100, but may allow the passage of air and sterilizing media to contact portable device 100. Sterilizing media may include, but is not limited to, ethylene oxide (ETO), steam, gamma irradiation, and electron beam (eBeam), and may help to maintain a sterile environment for portable device 100 prior to use. It should be appreciated that the sterile environment may provide sterile asepsis to eliminate microorganisms from the portable device. It should further be appreciated that package 700, first tray 300 and second tray 500 may be made of material including, but not limited to, paper, laminated film, plastic, and foil that may provide a sterile barrier. It should be appreciated that third connecting cable (FIG. 3) and sixth connector 650 may detach from package 700.

It should be appreciated that package 700 may form a second packaging that may facilitate safe storage and handling of portable device 100. It should be appreciated that package 700 may contain any number of trays or primary packages without departing from the present disclosure.

It should further be appreciated that when first connecting cable 210 is detached from portable device 100, portion 110 of portable device 100 may be charged using power supply 800 (FIG. 4) that may be connected to charging port 120 (FIG. 2 and FIG. 6) using a plurality of connecting cables. Portion 110 may be fully charged while remaining in a sealed and sterile environment. Fully charging portion 110 may include charging at least one chargeable battery to a full capacity and/or up to 100% of its capacity. It should be appreciated that portion 110 may be charged without removing cover 320, without removing cover 520, and/or without opening package 700. It should be appreciated that a power supply may be delivered to portable device 100 using components including, but not limited to, connecting cables, a wireless charging pad, an induction charge, an electromagnetic field, radio waves, resonance stimulation, and low level microwave stimulation. It should be appreciated that at least one chargeable battery may be securely enclosed within portable device 100 in a sterile environment without compromising the aseptic nature of the contents of portable device 100 according to embodiments of the present disclosure. It should be appreciated that any number of batteries may be provided in series, in a battery pack, and/or assembled any form without departing from the disclosure. It should further be appreciated that at least one chargeable battery may be provided inside portion 110, external to portion of portable device 110, and/or external to portable device 100 without departing from the present disclosure. It should also be appreciated that batteries may include, but are not limited to, rechargeable batteries, storage batteries, a secondary cell, and/or an accumulator that can be charged, discharged, and recharged any number of times.

Figure 6:
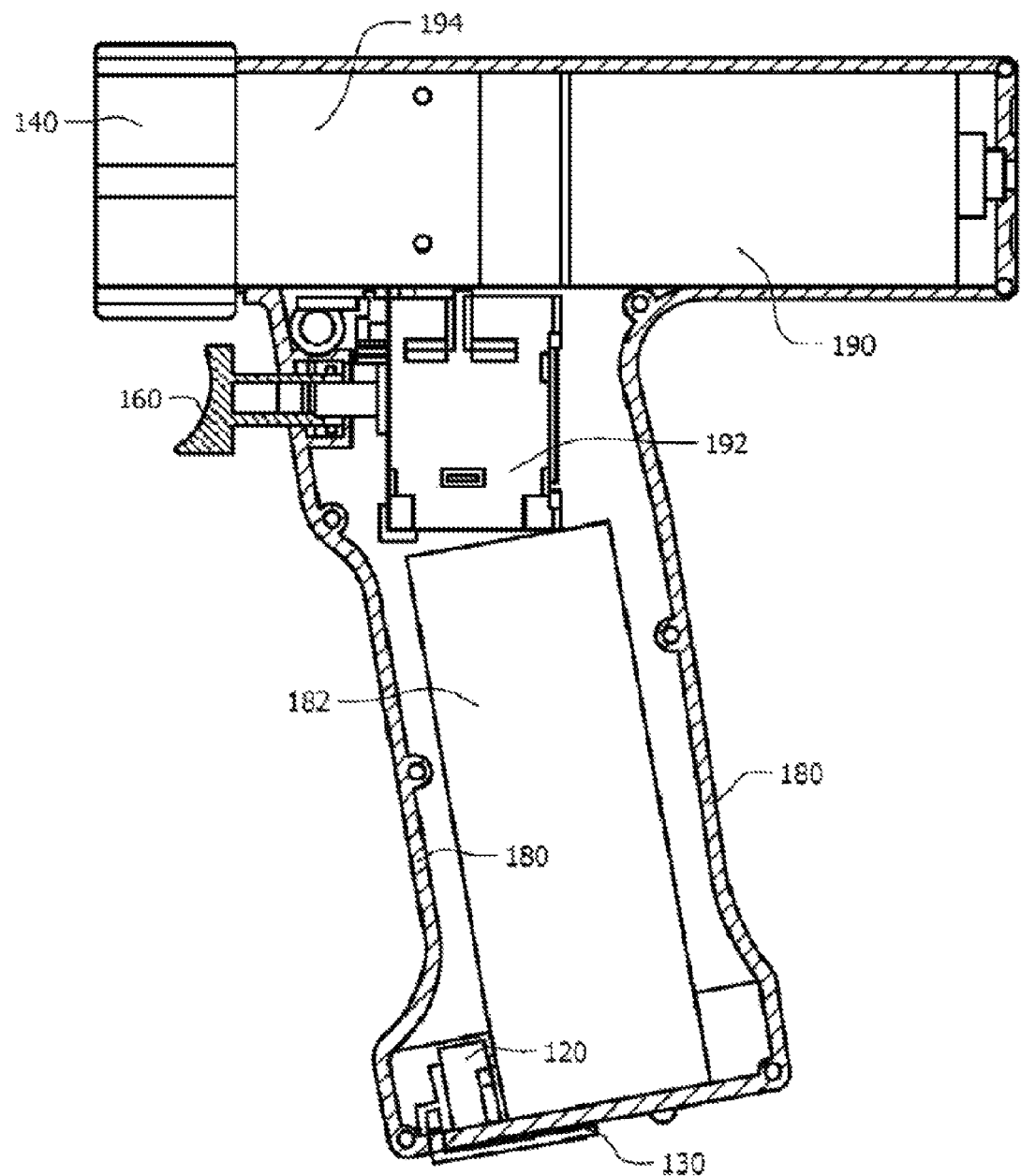
FIG. 6 depicts a sectional view of a portion of the portable device according to an embodiment of the present disclosure.

According to an embodiment of the present disclosure, as shown in FIG. 1, portion 110 of portable device 100 may provide attachment release ring 140, attachment coupling 150, and trigger 160. Attachment release ring 140 may rotate to a locked position and an unlocked position in embodiments of the present disclosure. Lock 170 may be provided to set attachment release ring 140 in the locked or in the unlocked position. It should be appreciated that lock 170 may be provided to lock the interior of attachment coupling 150 so that attachment coupling 150 may rotate in a clockwise direction or in a counterclockwise direction without departing from the present disclosure. It should be appreciated that a spring-loaded collar may be included in portable device 100 and may engage an attachment. It should further be appreciated that a spring-loaded collar may be pulled backwards along a central axis of portion 110, and when the spring-loaded collar is released, it may spring forward and securely hold the attachment in place. It should also be appreciated that an attachment may automatically engage with internal drive shaft 194 (FIG. 6). It should be appreciated that an attachment may be removed from attachment coupling 150 by pulling a spring-loaded collar backwards along a central axis of portion 110, and may provide for easily removing the attachment. Trigger 160 may be provided to vary the speed of rotation of the interior of attachment coupling. It should be appreciated that trigger 160 may be provided to control the direction of rotation of the interior of attachment coupling 150 in a clockwise direction or in a counterclockwise direction without departing from the present disclosure. It should be appreciated that portion 110 may provide a variable-speed trigger and an instant-reverse trigger in some embodiments of the present disclosure. Portion 110 may also provide at least one grip 180 that may stabilize portion 110 in the user's hands without departing from the present disclosure. It should be appreciated that the at least one grip 180 may be textured.

Figure 2:
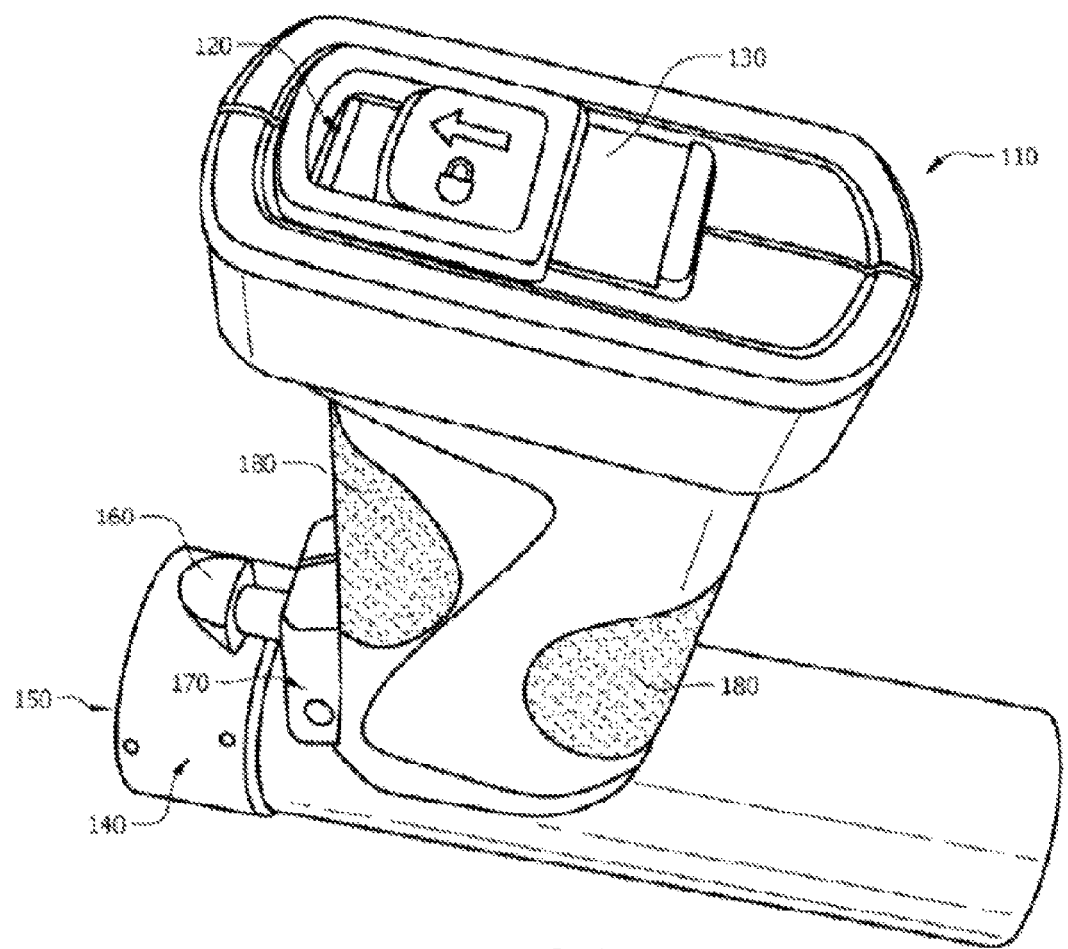
FIG. 2 depicts a perspective view of a portion of the portable device according to an embodiment of the present disclosure.

As shown in FIG. 2 according to an embodiment of the present disclosure, portion 110 may provide charging port 120 and charging port cover 130. Charging port 120 may include a female port that may be provided to receive first connector 230 (FIG. 1 and FIG. 5), and charging port 120 may be covered and protected by charging port cover 130. It should be appreciated that a female port may include, but is not limited to, a female USB port, a female cord end, and/or female wire end without departing from the present disclosure. It should be appreciated that charging port cover 130 may slide between a locked position and unlocked position 130 in embodiments of the present disclosure. It should be appreciated that the locked position may prevent first connecting cable 210 (FIG. 1 and FIG. 5) or another cable from attaching to charging port 120.

According to an embodiment of the present disclosure, as shown in FIG. 3, fourth connector 450 may receive fifth connector 630. Fifth connector 630 may include a male connector and may be provided at fifth end 620 of connecting cable 610. Sixth connector 650 may be provided at sixth end 640 of connecting cable 610 and may include a female port that may be accessible from an exterior of package 700 using sixth connector 650. Wall 710 of package 700 may house sixth connector 650. It should be appreciated that package 700 may include at least one pre-installed connecting cable without departing from the present disclosure.

Figure 4:
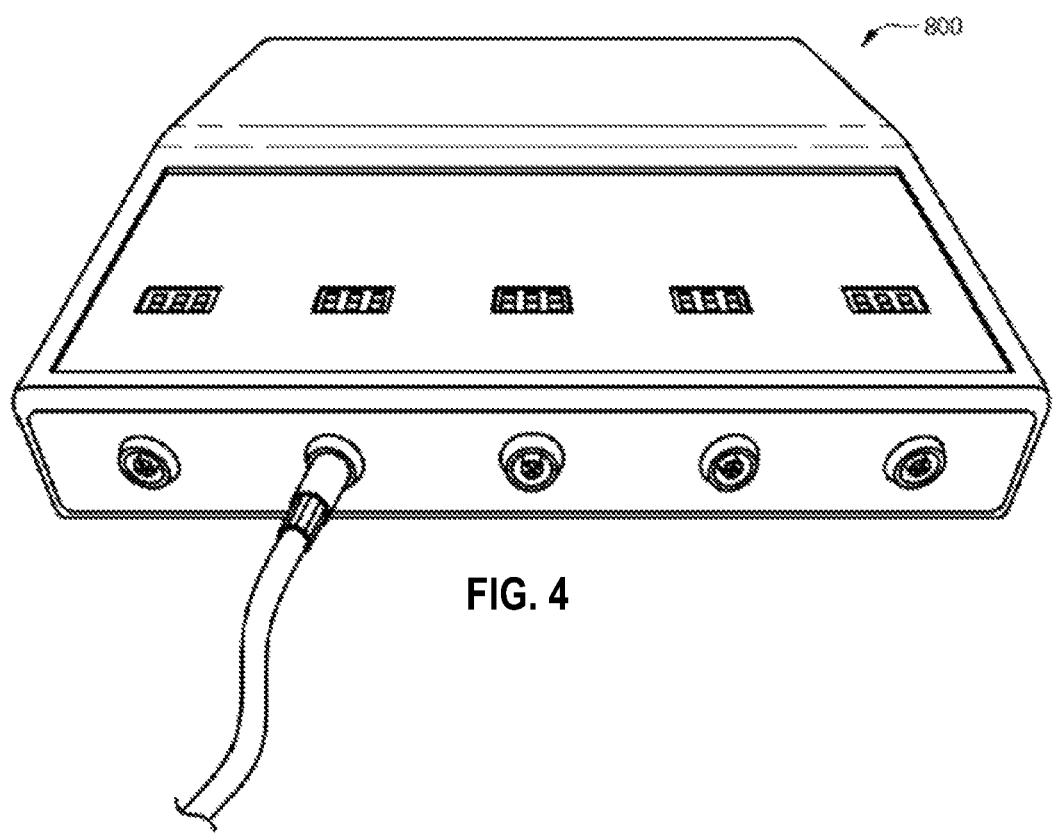
FIG. 4 depicts a power supply according to an embodiment of the present disclosure.

According to an embodiment of the present disclosure, as shown in FIG. 4, power supply 800 may be connected to the portable device and may read the charge level of the batteries. Power supply 800 may shut down when a full charge is reached, and may indicate to the user when portion 110 has attained a full charge, such as through an LED window. It should be appreciated that power supply 800 may be a battery charger in some embodiments of the present disclosure. It should be appreciated that any type of display window may be incorporated into power supply 800 without departing from the present disclosure. It should be appreciated that the charge level may indicate whether portion 110 is charged to a full capacity. It should be appreciated that a power supply may be provided within the sterile environment or external to the sterile environment according to embodiments of the present disclosure.

Figure 5:
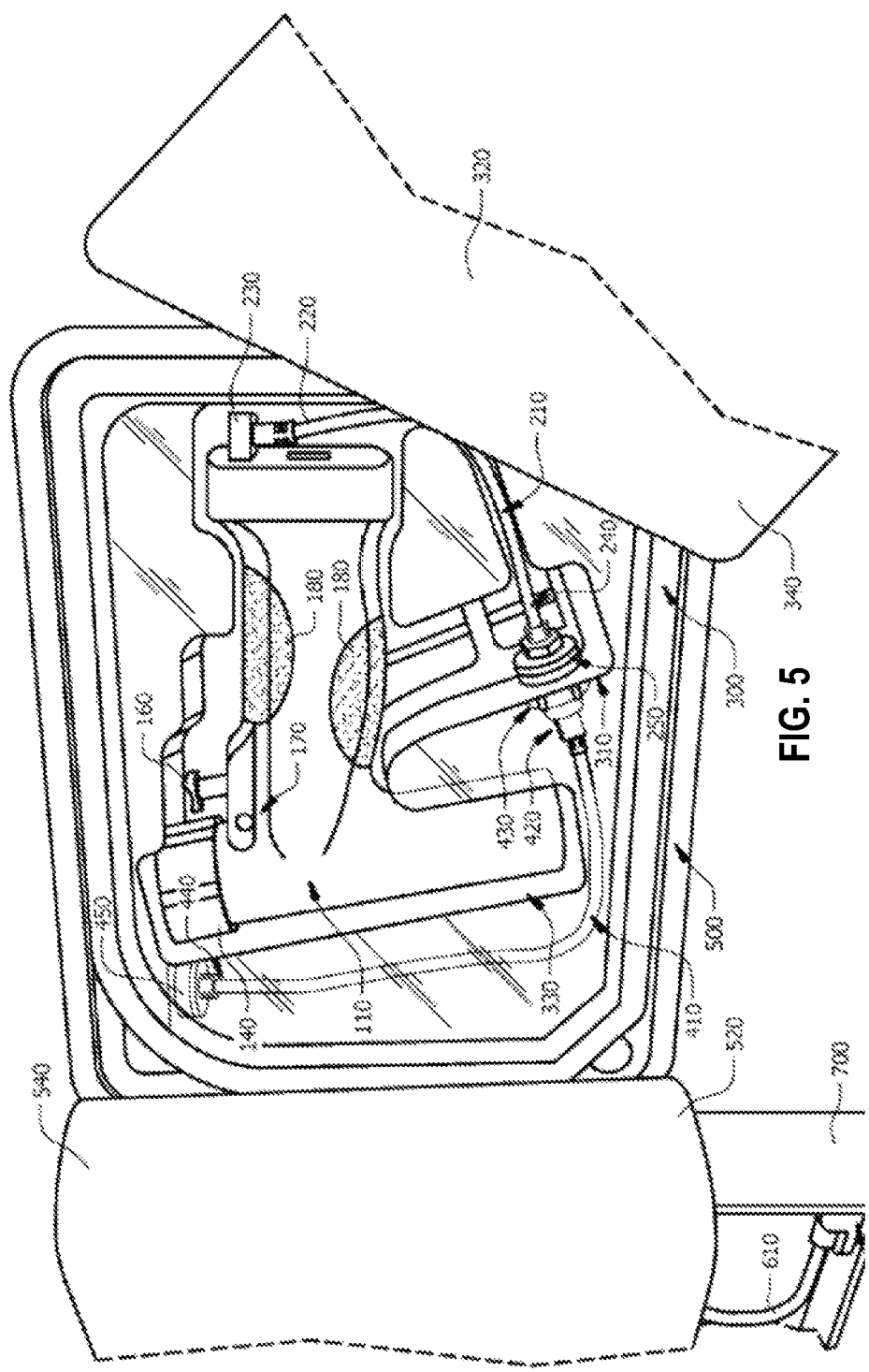
FIG. 5 depicts a portable device including open microbial barriers according to an embodiment of the present disclosure.

As shown in FIG. 5 according to an embodiment of the present disclosure, a portable device may provide cover 320 and cover 520 that may be opened and/or removed from first tray 300 and second tray 500, respectively. After removing cover 320 and cover 520, a user may remove portion 110 from compartment 330 and use portion 110 as desired. It should be appreciated that portion 110 may be removed from compartment 330 with up to 100% supply of power. It should further be appreciated that portion 110 may be charged when removed from compartment 330 without departing from the present disclosure.

As shown in FIG. 6 according to an embodiment of the present disclosure, portion 110 may provide battery 182. Battery 182 may be arranged inside of portion 110 and may be charged by connecting a cable to charging port 120. Portion 110 may include motor 190 and control panel 192. Motor 190 may control the speed of attachments that may be provided inside of attachment coupling 150. Control panel 192 may provide the electrical components required to operate at least trigger 160, motor 190, and attachment coupling 150. Internal drive shaft 194 may be connected to attachment coupling 150 and provide for an engagement of portable device 100 with an attachment. It should be appreciated that an engagement with an attachment may be accomplished using a spring-loaded collar without departing from the present disclosure.

It should be appreciated that each end of each connecting cable may be secured within a respective wall or package using mechanically compressed seals, glue, and/or a similar sealing agent that may be provided to maintain microbe-free connections. It should be appreciated that attachment coupling 150 may be provided to receive an attachment. It should be appreciated that an attachment may be selected from a plurality of attachment types and inserted into attachment coupling 150. The plurality of attachment types may include, but are not limited to, saw blades, wire/pin drivers, and drill chucks. It should further be appreciated that an attachment may be inserted into attachment coupling 150 when lock is in use. The end of the attachment provided inside of attachment coupling 150 may engage an interior of attachment coupling 150 and maintain a secured position. It should be appreciated that a free end of the attachment that is opposite of the end of attachment disposed within attachment coupling 150 may be pulled slightly to ensure that the attachment is secured inside of attachment coupling 150.

It should be appreciated that when attachment release ring 140 is rotated to unlocked position, an attachment may be removed by pulling the attachment away from attachment coupling 150. It should be appreciated that when the portable device is locked, injury to patients may be prevented. When coupling attachments, removing attachments, and/or before laying the portable device down, the portable device may be locked and may prevent injury to a user and/or patient.

It should be appreciated that portion 110 and any attachments thereto may cool down following a maximum time of constant use. The maximum time of constant use and a minimum time of non-use may be predetermined time periods. For example, the maximum time of constant use for drilling may be 60 seconds, and the minimum time of non-use may be 60 seconds over nine cycles. Regarding sawing, for example, the maximum time of constant use for drilling may be 30 seconds, and the minimum time of non-use may be 60 seconds over nine cycles. It should be appreciated that additional portable devices may be used if extended periods of constant use are required. It should be appreciated that the temperature of portable device 100 may be controlled and may prevent overheating of the device and harm to patients.

It should be appreciated that portable device 100 may be a battery-driven tool system that may be used for medical procedures including, but not limited to, drilling, reaming, pin and wire placement, and cutting bone and hard tissue. It should be appreciated that portable device 100 may be operated for non-medical use including, but not limited to, construction, household-use, and food preparation. It should be appreciated that portable device 100 may provide power for immediate use after opening cover 320, cover 520, and/or package 700. It should be appreciated that portable device 100 may provide cost advantages over reusable portable devices. It should further be appreciated that a portable device according to embodiments of the present disclosure may be used one time and may be recycled and/or discarded after use. It should be appreciated that portable device 100 may eliminate a need for maintenance and lubrication. It should also be appreciated that a portable device according to embodiments of the present disclosure may eliminate a need for back-up batteries and/or a back-up power supply. It should further be appreciated that portable device 100 may not require special processes for cleaning and/or disposal of any component.

Figure 7:
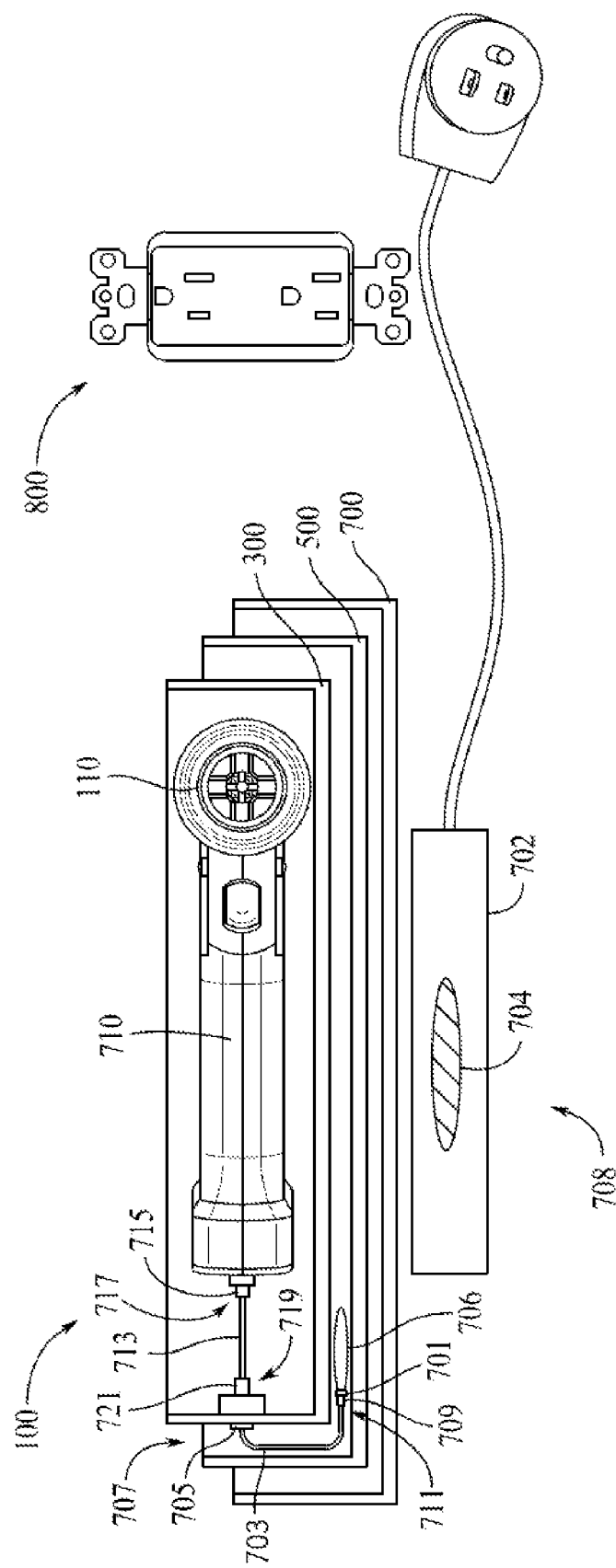
FIG. 7 depicts a top view of a portable device and a wireless charging station utilizing induction charging according to an embodiment of the present disclosure.

As shown in FIG. 7 according to an embodiment of the present disclosure, a portable device 100 may have a wireless charging station 708 using an induction charge to charge the at least one chargeable battery 710 wirelessly. The wireless charging station 708 may include a sender coil 704 secured in a charging plate 702 and operable to induce a magnetic field using an AC current. A receiver coil 706 may be secured in the second tray 500 of the portable device 100 and operable to receive and convert the AC current into a DC current. The receiver coil 706 may include a receiver connector 701 operably coupled to a relay cable 703 secured in the first tray 300. The receiver connector 701 may include a male connector provided at an end of the receiver coil 706.

The first relay cable 703 may have a first relay connector 705. The first relay connector 705 may include a male connector provided at a first end 707 of the first relay cable 703 operably coupled to a second relay cable 713. It should be appreciated that the male connector may be a universal serial bus (USB), a male cord end, and/or male wire end without departing from the present disclosure. A second relay connector 709 of the first relay cable 703 may be provided at a second end 711 opposite the first end 707. The second relay connector 709 may include a female port that may be provided to receive the receiver connector 701 of the receiver coil 706. It should be appreciated that the female port may include, but is not limited to, a USB port, a female cord end, and/or female wire end without departing from the present disclosure.

The second relay cable 713 may have a first relay connector 715. The first relay connector 715 may include a male connector provided at a first end 717 of the second relay cable 713. The male connector may be received in the female port of the charging port 120, operably coupling the second relay cable 713 to the at least one chargeable battery 710. A second relay connector 721 of the second relay cable 713 may be provided at a second end 719 opposite the first end 717, and the second end 719 may be secured within the first wall 310 of the first tray 300. The second relay connector 721 may include a female port that may be provided to receive the first relay connector 705 of the first relay cable 703. The power is delivered from the receiver coil 706 to the at least one chargeable battery 710 via the first relay cable 703 and the second relay cable 713.

It should be appreciated that the receiver coil 706 may be located within the portion 110 of the device 100 if the receiver coil 706 is within an air gap of the sender coil 704. Alternatively the receiver coil 706 may be located anywhere within or exterior to the packaging 700, but nearer to the sender coil 704, if the air gap is too wide to the device 100 to guarantee a sufficiently strong signal, in which case a relay cable or cables can be employed to complete the connection.

Figure 8:
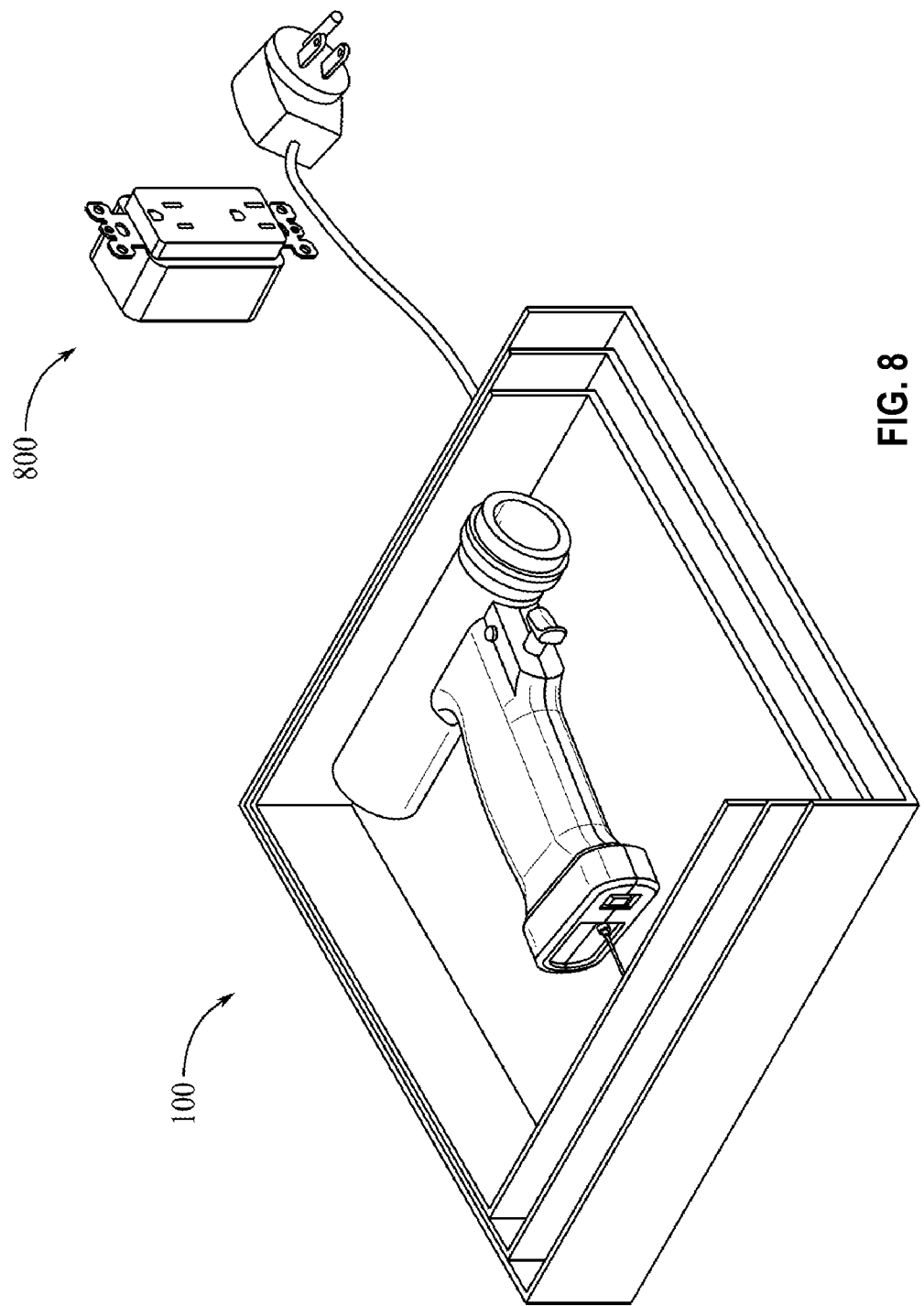
FIG. 8 depicts a top isometric view of a portable device and a wireless charging station utilizing induction charging according to an embodiment of the present disclosure.

FIG. 8 illustrates the portable device 100 charging via induction charging wherein the portable device 100 can be simply placed on top of the charging plate 702 (not visible) for charging. Once the portable device 100 is charged, the portable device can be simple picked up or removed from the charging plate 702.

Figure 9:
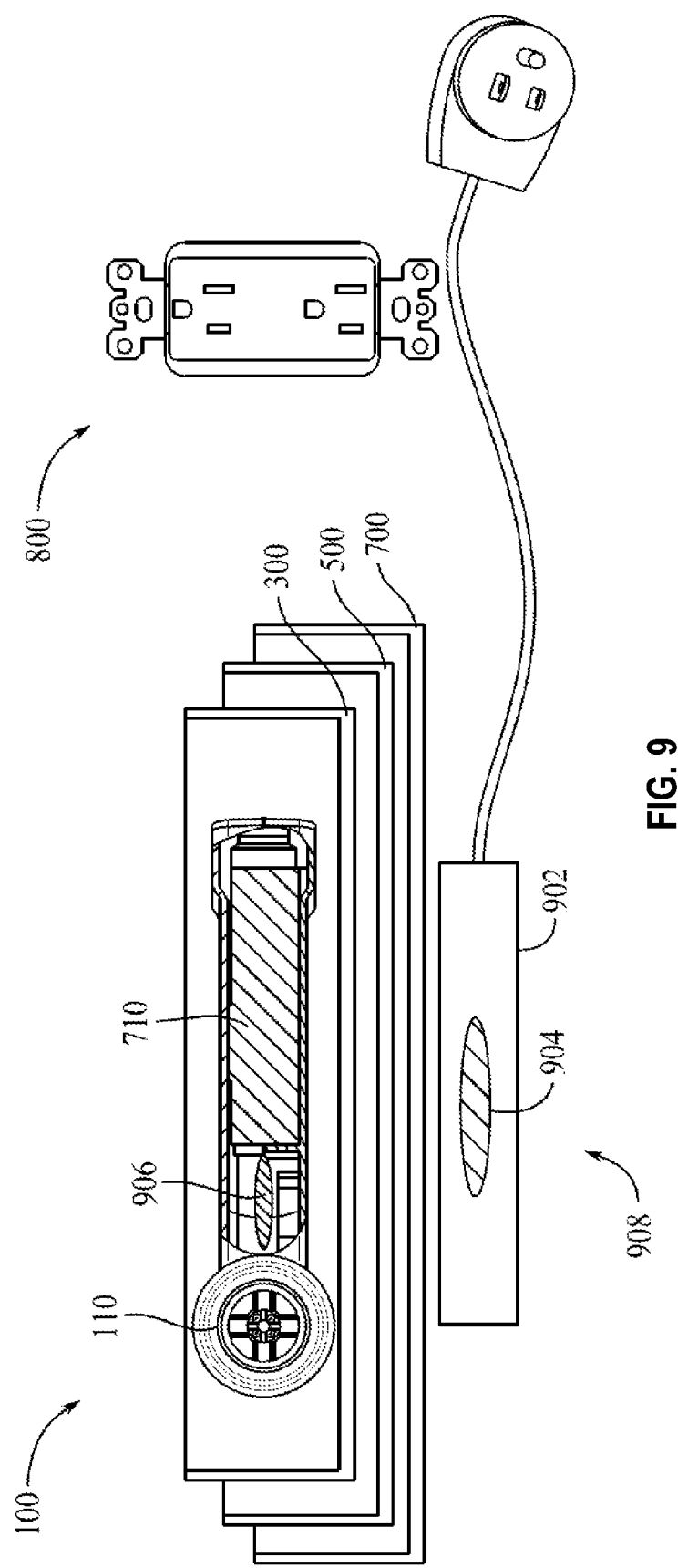
FIG. 9 depicts a top view of a portable device and a wireless charging station utilizing magnetic resonance charging according to an embodiment of the present disclosure.

As shown in FIG. 9 according to an embodiment of the present disclosure, a portable device 100 may have a wireless charging station 908 using magnetic resonance to charge the at least one chargeable battery 710 wirelessly. The wireless charging station 908 may include a sender coil 904 secured in a charging plate 902 operable to induce an oscillating magnetic field using an oscillating AC current. A receiver coil 906 may be secured in the portion 110 of the portable device 100 and operable to receive and convert the oscillating AC current into a DC current. It should be appreciated that the receiver coil 906 may be positioned anywhere within or outside the portable device 100. For example, the receiver coil 906 may be secured within the second tray 500, the first tray 300, the package 700 or may be secured outside the package 700 without deviating from the scope of the present disclosure.

Figure 10:
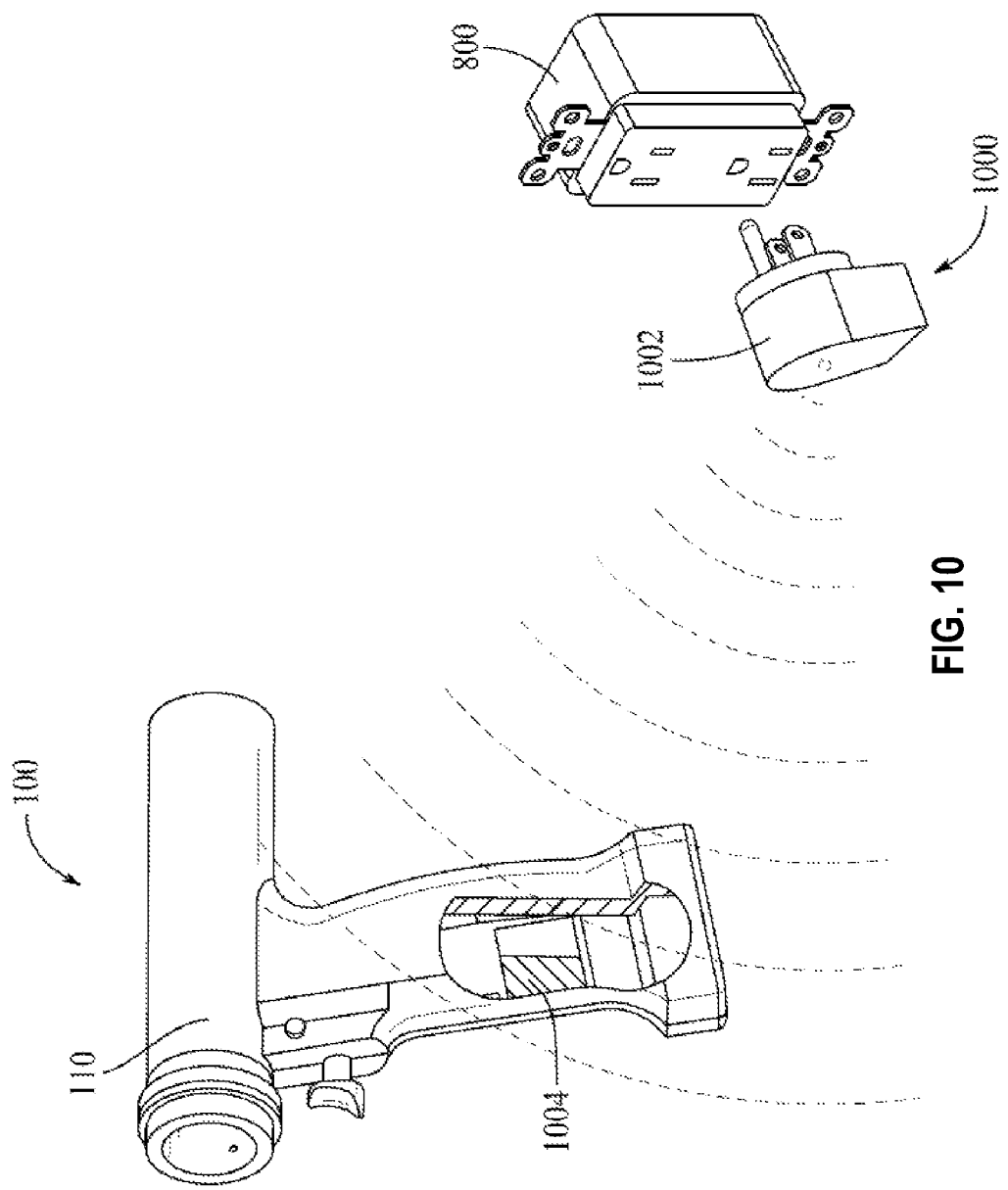
FIG. 10 depicts a top view of a portable device and a wireless charging station utilizing radio frequency charging according to an embodiment of the present disclosure.

As shown in FIG. 10 according to an embodiment of the present disclosure, a portable device 100 may have a wireless charging station 1000 using radio frequency to charge the at least one chargeable battery 710 wirelessly. The wireless charging station 1000 may include a radio frequency transmitter 1002 operable to send a low-wattage radio wave signal. A radio frequency receiver 1004 may be secured in the portion 110 of the portable device 100 and operable to receive and convert the signal into a DC current to charge the at least one chargeable battery 710. It should be appreciated that the radio frequency receiver may be positioned anywhere within or outside the portable device 100. For example, the radio frequency receiver may be positioned within the second tray 500, within the first tray 300, within the package 700, or outside the package 700 without deviating from the scope of the present disclosure.

Figure 11:
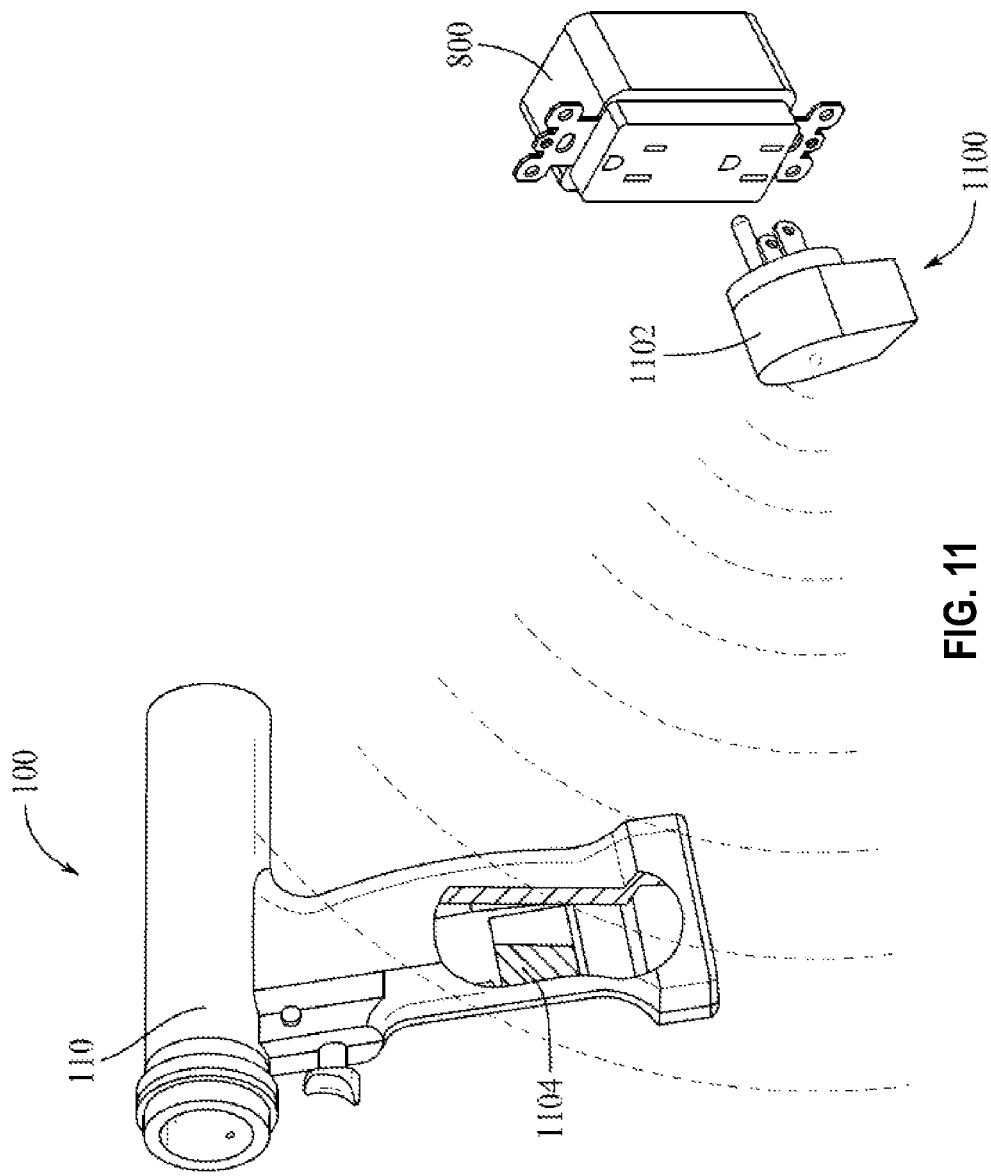
FIG. 11 depicts a top view of a portable device and a wireless charging station utilizing microwave stimulation charging according to an embodiment of the present disclosure.

As shown in FIG. 11, a portable device 100 may have a wireless charging station 1108 using microwave stimulation to charge the at least one chargeable battery 710 wirelessly. The wireless charging station 1108 may include a microwave emitter 1102 operable to send microwaves. A rectenna 1104 comprising a combined antenna and rectifier may be secured in portion 110 of the portable device 100 and operable to receive and convert the microwave into a DC current. It should be appreciated that the rectenna 1104 may be positioned anywhere within or outside the portable device 100. For example, the rectenna 1104 may be positioned within the second tray 500, the first tray 300, the package 700, or outside the package 700 without deviating from the scope of the present disclosure.

Figure 12:
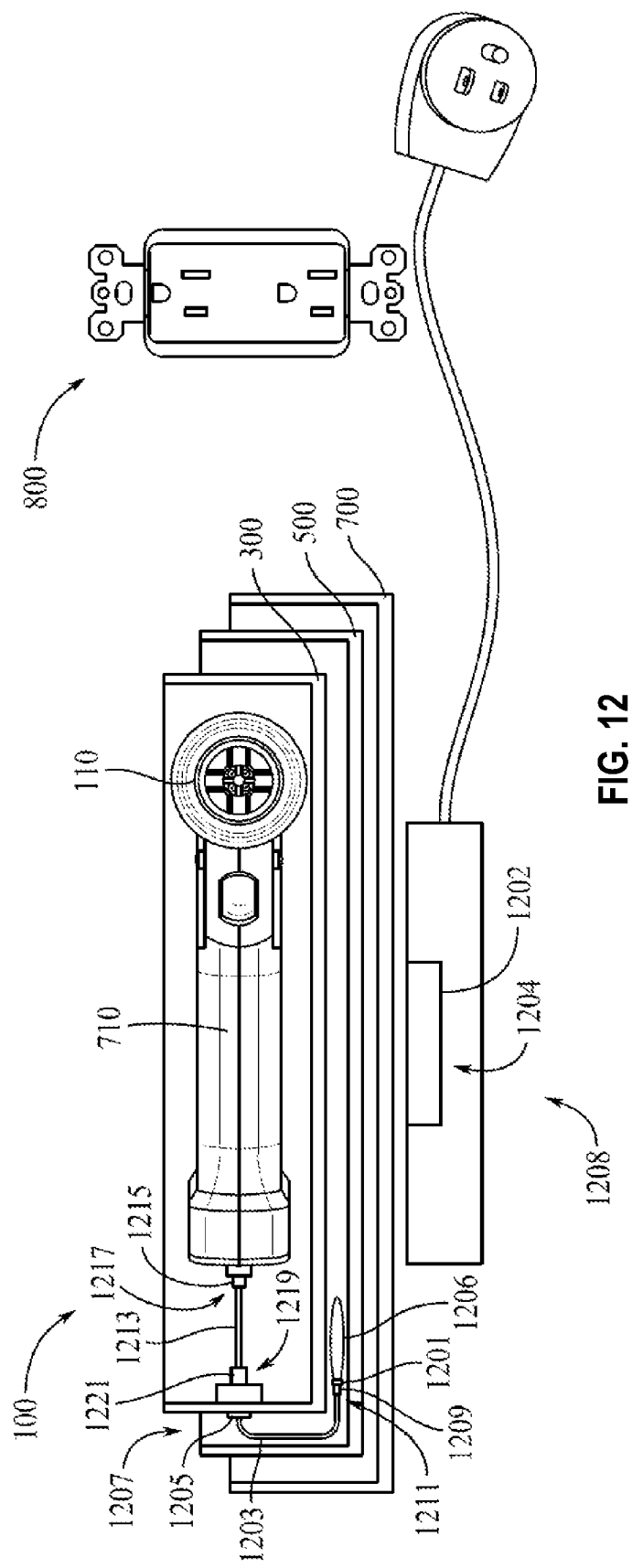
FIG. 12 depicts a top view of a portable device and a wireless charging station utilizing capacitive coupling according to an embodiment of the present disclosure.

As shown in FIG. 12, a portable device 100 may have a wireless charging station 1208 using capacitive coupling to charge the at least one chargeable battery 710 wirelessly. The wireless charging station 1208 may include a transmitter 1204 in the form of a transmitter patch 1202. A receiver may be secured on the package 700 and may be in the form of a receiver patch 1206. The transmitter 1204 is operable to transmit power to the receiver when the transmitter patch 1202 and the receiver patch 1206 are positioned proximate to each other to effectively form a capacitor with the intervening space acting at a dielectric. The receiver patch 1206 may include a receiver connector 1201 operably coupled to a first relay cable 1203 secured in the second tray 500. The receiver connector 1201 may include a male connector provided at an end of the receiver.

The first relay cable 1203 may have a first relay connector 1205. The first relay connector 1205 may include a male connector provided at a first end 1207 of the first relay cable 1203 operably coupled to a second relay cable 1213. It should be appreciated that the male connector may be a universal serial bus (USB), a male cord end, and/or male wire end without departing from the present disclosure. A second relay connector 1209 of the first relay cable 1203 may be provided at a second end 1211 opposite the first end 1207. The second relay connector 1205 may include a female port that may be provided to receive the receiver connector 1201 of the receiver patch 1206. It should be appreciated that the female port may include, but is not limited to, a USB port, a female cord end, and/or female wire end without departing from the present disclosure.

The second relay cable 1213 may have a first relay connector 1215. The first relay connector 1215 may include a male connector provided at a first end 1219 of the second relay cable 1213. The male connector may be received in the female port of the charging port 120, operably coupling the second relay cable 1213 to the at least one chargeable battery 710. A second relay connector 1221 of the second relay cable 1213 may be provided at a second end 1217 opposite the first end 1219, and the second end 1217 may be secured within the first wall 310 of the first tray 300. The second relay connector 1221 may include a female port that may be provided to receive the first relay connector 1205 of the first relay cable 1203. The power is delivered from the receiver patch 1206 to the at least one chargeable battery 710 via the first relay cable 1203 and the second relay cable 1213.

Figure 13:
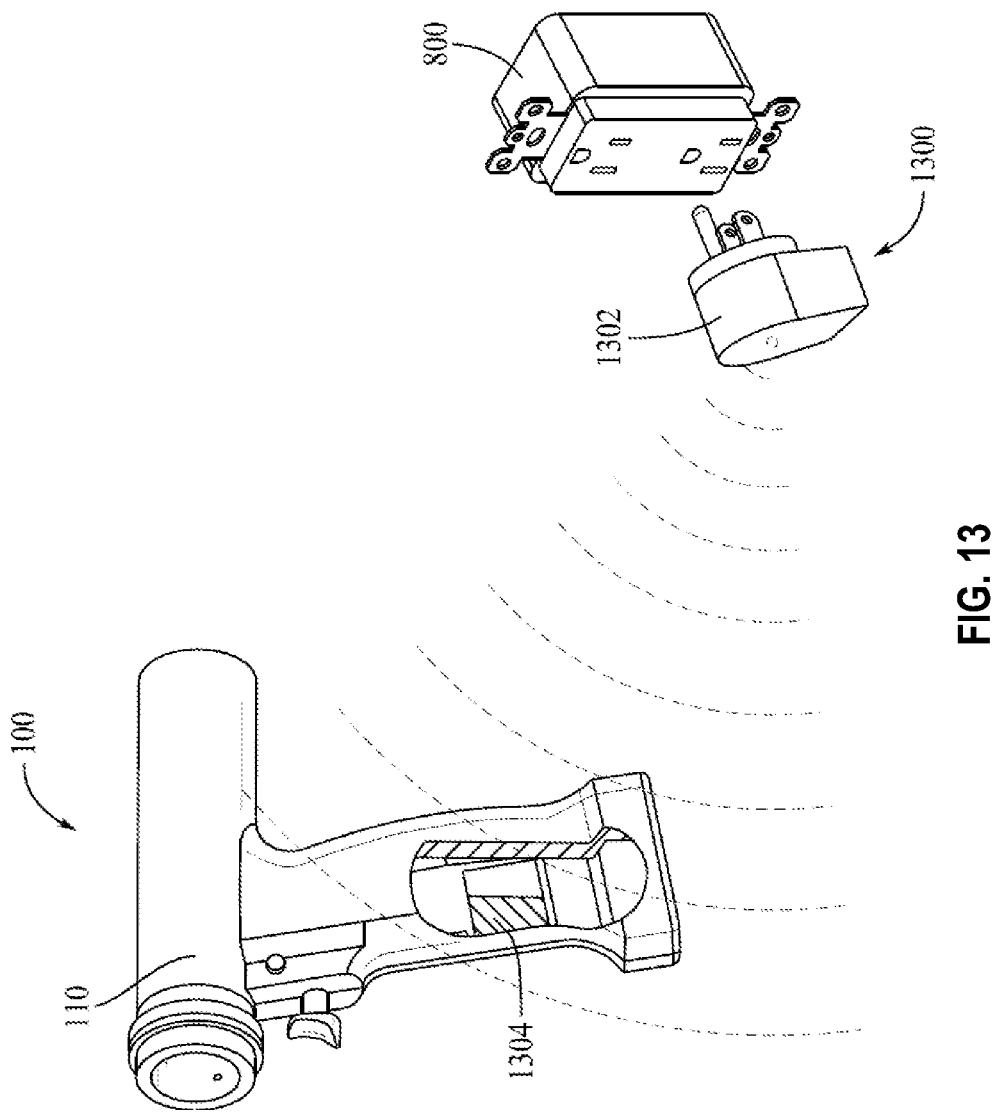
FIG. 13 depicts a top view of a portable device and a wireless charging station utilizing ultrasonic charging according to an embodiment of the present disclosure.

As shown in FIG. 13, a portable device 100 may have a wireless charging station 1300 using ultrasonic charging to charge the at least one chargeable battery 710 wirelessly. The wireless charging station 1300 may include an ultrasonic transmitter 1302 operable to transmit energy via ultrasonic waves. An ultrasonic receiver 1304 may be positioned in the portion 110 of the portable device 100 and operable to receive and convert the ultrasonic waves into a DC current. It should be appreciated that the ultrasonic receiver 1304 may be positioned anywhere within or outside the portable device 100. For example, the ultrasonic receiver 1304 may be positioned within the second tray 500, the first tray 300, the package 700, or outside the package 700 without deviating from the scope of the present disclosure.

It should be appreciated that a wireless charging station may charge more than one portable device 100 at a time. It should also be appreciated that the wireless charging station does not require the portable device 100 to be physically coupled to the wireless charging station and may provide convenience as the portable device 100 can be simply placed on top of the wireless charging station to charge the at least one chargeable battery 710. Furthermore, a lack of cables may also provide convenience as less space is needed to store the portable device 100 while it is charging.

Figure 14:
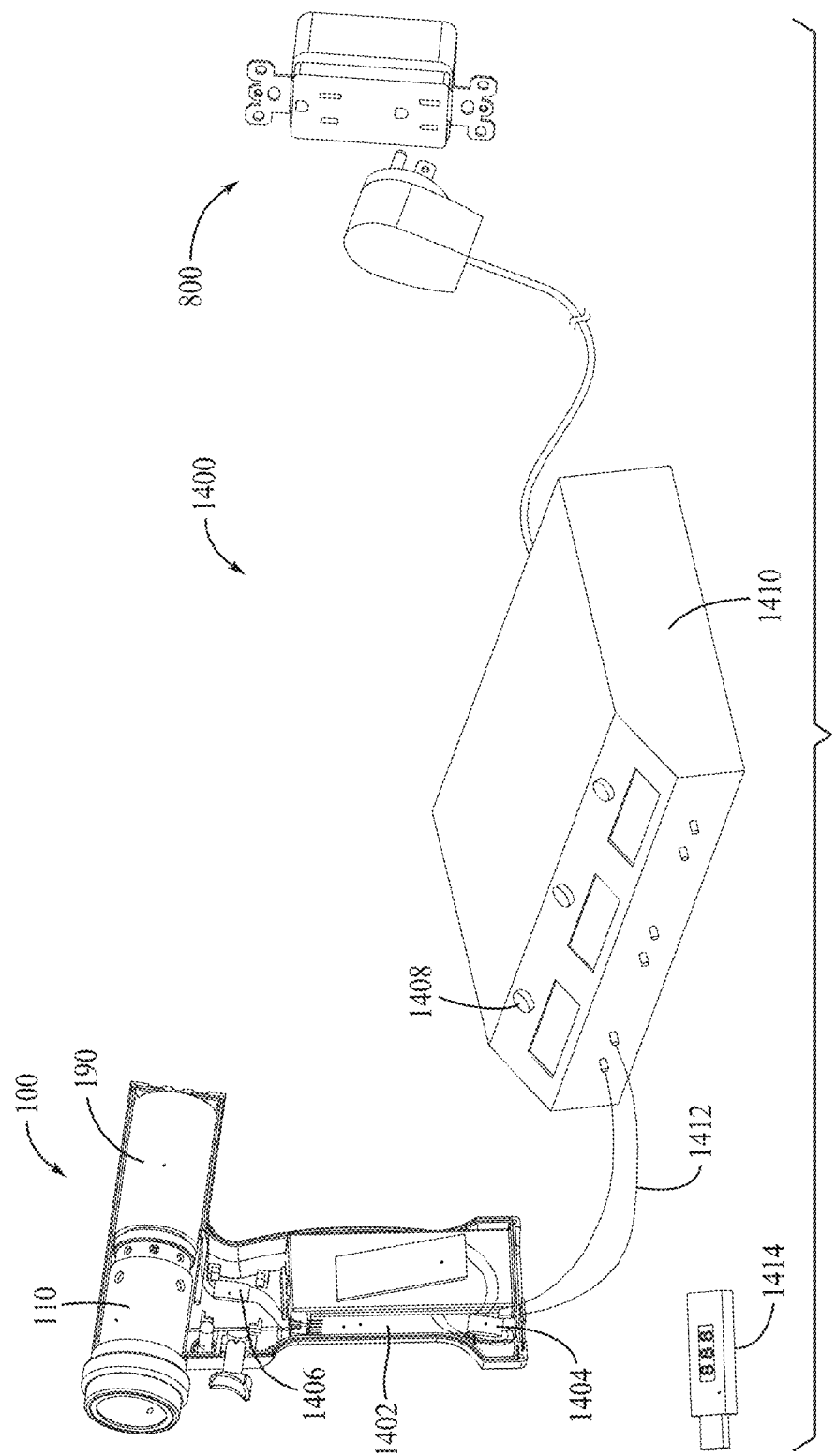
FIG. 14 depicts an intelligent charging system according to an embodiment of the present disclosure.

As shown in FIG. 14 according to an embodiment of the present disclosure, a portable device 100 may have an intelligent or smart charging system 1400 operable to monitor and maintain the at least one chargeable battery 710. The intelligent charging system 1400 may include a chip or a PCB 1402 operable to control a charge current to the at least one chargeable battery 710. The chip 1402 may be programmed to dissipate the charge current when the at least one chargeable battery 710 is full. The chip 1402 may also be programmed to provide a cut-off to the charge current to prevent damage to the at least one chargeable battery 710. The chip 1402 may also be programmed to maintain a temperature of the at least one chargeable battery 710 within a range of safe temperatures.

The intelligent charging system 1400 may further include a fuse 1404 operable to turn off or disconnect the at least one chargeable battery 710 from the power supply 800 during a fuse triggering event. The fuse triggering event may be, for example, when the at least one chargeable battery 710 receives too much power from the power supply 800, which may damage the at least one chargeable battery 710. The intelligent charging system 1400 may further include a thermal fuse 1406 operable to monitor a temperature of the motor 190 and power off the motor 190 if the temperature is greater than a threshold temperature. The fuse 1404 and the thermal fuse 1406 may be operable to be reset and reused. For example, the fuse 1404 or the thermal fuse 1406 can utilize a thermal limit wherein the fuse 1404 will disconnect the at least one chargeable battery 710 from the power supply 800 if the fuse 1404 reaches a specified temperature.

The intelligent charging system 1400 may further include a trigger 1408 operable to prevent unauthorized use or charging of the portable device 100 without authorization. The trigger 1408 may be located anywhere within or external to the device 100 or the package 700 or may be located on a monitor 1410. For example, the trigger 1408 may be used to restrict fuse resetting to authorized users. Authorization may be provided via, for example, a keypad, lock, fingerprint reader, code, or password. After authorization, the fuse 1404, thermal fuse 1406, and/or the chip or PCB 1402 may be reset.

The intelligent charging system 1400 may further use a charging cable 1412 operable to charge the device 100 and to transfer data two ways from the at least one chargeable battery 710 to the monitor 1410 and/or a controller to monitor the at least one chargeable battery 710. The charging cable 1412 may be the first, second, and third connecting cables 210, 410, 610 previously described. The monitor 1410 can be located on the package 700 and display battery information such as battery charge, estimated time to full charge, temperature, or the like. The monitor 1410 may be operable to charge the at least one chargeable battery 710 and/or reset the fuse 1404, thermal fuse 1406, and/or the chip or PCB 1402. It should be appreciated that the monitor 1410 can be located anywhere within or external the portable device 100 and can receive or send commands to the controller, chip, or PCB 1402 via a wired or wireless connection. The intelligent charging system 1400 may also include a portable monitor 1414 operable to monitor and display a status of the at least one chargeable battery 710. The portable monitor 1414 may be in the form of a USB stick or the like.

In at least one example, the package 700 can include a plurality of portable devices 100. One or more of the plurality of portable devices 100 can be received in a first tray and a second tray as discussed above. In some examples, a first tray can receive and secure a plurality of portable devices. In some examples, a plurality of first trays can each receive and secure one or more of the plurality of portable devices. First microbial barriers can each be arranged to seal corresponding first trays and maintain a sterile environment for the portable devices. For example, if only one first tray is included to receive a plurality of portable devices, only one first microbial barrier is included corresponding to the first tray. In at least one example, the chargeable batteries can be arranged inside of the portable devices. In some examples, the chargeable batteries can be arranged external to the portable devices and contained within the corresponding first trays. Second trays can each be operable to receive and secure corresponding first trays in the second trays. In some examples, a plurality of first trays may be received in one second tray. In some examples, one second tray may receive one first tray. Second microbial barriers can each be arranged to seal corresponding second trays and maintain a sterile environment for each of the portable devices. For example, if only one second tray is included, only one second microbial barrier is included corresponding to the second tray. If more than one second tray is included, more than one second microbial barriers can be included corresponding to the number of second trays. A package can receive one or more second trays and provide a sterile enclosure for the plurality of portable devices. Any combination of portable devices, first trays, and second trays can be included in the package. For example, the package, as discussed above, may include any number and/or combination of: (i) one first tray which is received in one second tray, (ii) a plurality of first trays received in one second tray. Within each of the first trays can include one or more portable devices. A power supply can be electrically connected with each of the portable devices such that the chargeable batteries of each of the portable devices are charged in the sterile environment.

In some examples, more than one portable device 100 can be received in a single first tray which is then received in a second tray. The package 700, along with any configuration of portable devices 100, first tray(s), and/or second tray(s), provides a sterile environment to charge the portable devices 100 either individually, together all at the same time, or any combination of portable devices 100. For example, the power supply can provide a charge to all of the portable devices until all of the portable devices are fully charged or charged to the desired amount. In some examples, the power supply can provide a charge to the portable devices as needed for each individual portable device.

The power supply can supply power to the chargeable batteries corresponding with the portable devices via any charging method and/or system as discussed herein. For example, the power supply can supply power to each of the chargeable batteries corresponding with the portable devices via a wireless charging station located external to the portable devices having a transmitter operable to transmit power wirelessly to a receiver secured in each of the portable devices. In some examples, the power supply can supply power to each of the chargeable batteries corresponding with the portable devices via wired connection. For example, the system can include a plurality of first connecting cables and a plurality of second connecting cables electrically connected to corresponding first connecting cables. The first connecting cables can be secured within the first trays and the second connecting cables can be secured within the first trays and the second trays. The power supply can be electrically connected with the second connecting cable to supply power to each of the chargeable batteries corresponding with the portable devices.

The charging method, i.e. wirelessly or wired, can be different between individual portable devices. In some examples, the charging method can be the same for all of the plurality of portable devices.

A charging system, for example charging system 1400 discussed herein, can maintain the chargeable batteries. The charging system can include a chip or a PCT to control a charge current to the chargeable batteries. In some examples, a fuse can be included to disconnect the chargeable batteries from the power supply when a fuse triggering event occurs. In some examples, each portable device or a combination of portable devices can be disconnected by corresponding one or more fuses. In some examples, one fuse can disconnect all of the plurality of portable devices at the same time.

In at least one example, the system can charge the plurality of portable devices intelligently to improve the lifespan and efficiency of the chargeable batteries. For example, the system can include a neural network to collect data and determine the time, length of charge, amount of power supplied, and other suitable aspects of charging the chargeable batteries. Also, the system can determine charge each portable device according to individual needs and requirements.

The neural network is a multi-layer deep learning network of interconnected nodes. Each node can represent a piece of information. Information associated with the nodes is shared among the different layers and each layer retains information as information is processed. In some cases, the neural network can include a feed-forward network, in which case there are no feedback connections where outputs of the network are fed back into itself. In some cases, the neural network can include a recurrent neural network, which can have loops that allow information to be carried across nodes while reading in input.

Information can be exchanged between nodes through node-to-node interconnections between the various layers. Nodes of the input layer can activate a set of nodes in the first hidden layer. For example, as shown, each of the input nodes of the input layer is connected to each of the nodes of the first hidden layer. The nodes of the hidden layer can transform the information of each input node by applying activation functions to the information. The information derived from the transformation can then be passed to and can activate the nodes of the next hidden layer, which can perform their own designated functions. Example functions include convolutional, up-sampling, data transformation, pooling, and/or any other suitable functions. The output of the hidden layer can then activate nodes of the next hidden layer, and so on. The output of the last hidden layer can activate one or more nodes of the output layer, at which point an output is provided. In some cases, while nodes (e.g., node) in the neural network are shown as having multiple output lines, a node has a single output and all lines shown as being output from a node represent the same output value.

In some cases, each node or interconnection between nodes can have a weight that is a set of parameters derived from the training of the neural network. For example, an interconnection between nodes can represent a piece of information learned about the interconnected nodes. The interconnection can have a numeric weight that can be tuned (e.g., based on a training dataset), allowing the neural network to be adaptive to inputs and able to learn as more data is processed.

The neural network can be pre-trained to process the features from the data in the input layer using the different hidden layers in order to provide the output through the output layer. In an example in which the neural network is used to identify objects in images, the neural network can be trained using training data that includes both images and labels. For instance, training images can be input into the neural network, with each training image having a label indicating the classes of the one or more objects in each image (basically, indicating to the network what the objects are and what features they have).

In some cases, the neural network can adjust the weights of the nodes using a training process called backpropagation. Backpropagation can include a forward pass, a loss function, a backward pass, and a weight update. The forward pass, loss function, backward pass, and parameter update is performed for one training iteration. The process can be repeated for a certain number of iterations for each set of training images until the neural network is trained enough so that the weights of the layers are accurately tuned.

For the example of identifying objects in images, the forward pass can include passing a training image through the neural network. The weights can be initially randomized before the neural network is trained. The image can include, for example, an array of numbers representing the pixels of the image. Each number in the array can include a value from 0 to 255 describing the pixel intensity at that position in the array. In one example, the array can include a 28×28×3 array of numbers with 28 rows and 28 columns of pixels and 3 color components (such as red, green, and blue, or luma and two chroma components, or the like).

For a first training iteration for the neural network, the output can include values that do not give preference to any particular class due to the weights being randomly selected at initialization. For example, if the output is a vector with probabilities that the object includes different classes, the probability value for each of the different classes may be equal or at least very similar (e.g., for ten possible classes, each class may have a probability value of 0.1). With the initial weights, the neural network is unable to determine low level features and thus cannot make an accurate determination of what the classification of the object might be. A loss function can be used to analyze errors in the output. Any suitable loss function definition can be used.

The loss (or error) can be high for the first training images since the actual values will be different than the predicted output. The goal of training is to minimize the amount of loss so that the predicted output is the same as the training label. The neural network can perform a backward pass by determining which inputs (weights) most contributed to the loss of the network, and can adjust the weights so that the loss decreases and is eventually minimized.

A derivative of the loss with respect to the weights can be computed to determine the weights that contributed most to the loss of the network. After the derivative is computed, a weight update can be performed by updating the weights of the filters. For example, the weights can be updated so that they change in the opposite direction of the gradient. A learning rate can be set to any suitable value, with a high learning rate including larger weight updates and a lower value indicating smaller weight updates.

The neural network can include any suitable deep network. One example includes a convolutional neural network (CNN), which includes an input layer and an output layer, with multiple hidden layers between the input and out layers. The hidden layers of a CNN include a series of convolutional, nonlinear, pooling (for downsampling), and fully connected layers. In other examples, the neural network can represent any other deep network other than a CNN, such as an autoencoder, a deep belief nets (DBNs), a Recurrent Neural Networks (RNNs), etc.

Neural network can also be used to perform deep learning. In this example, the neural network includes an input layer, a convolutional hidden layer, a pooling hidden layer, fully connected layers, and output layer. The neural network can identify specific environmental features (e.g., humidity, temperature, amount of charge, number of portable devices, etc.) in an image. First, each feature is considered as a neuron that has learnable weights and biases. Each neuron receives some inputs, performs a dot product and optionally follows it with a non-linearity function. The neural network can also encode certain properties into the architecture by expressing a single differentiable score function from the data on one end to class scores at the other to extract specific environmental features from the target image. After identifying features as specific environmental features, the neural network can generate a mean score (or z-score) of each feature and take the average of the scores within the user-defined buffer.

Figure 15A:
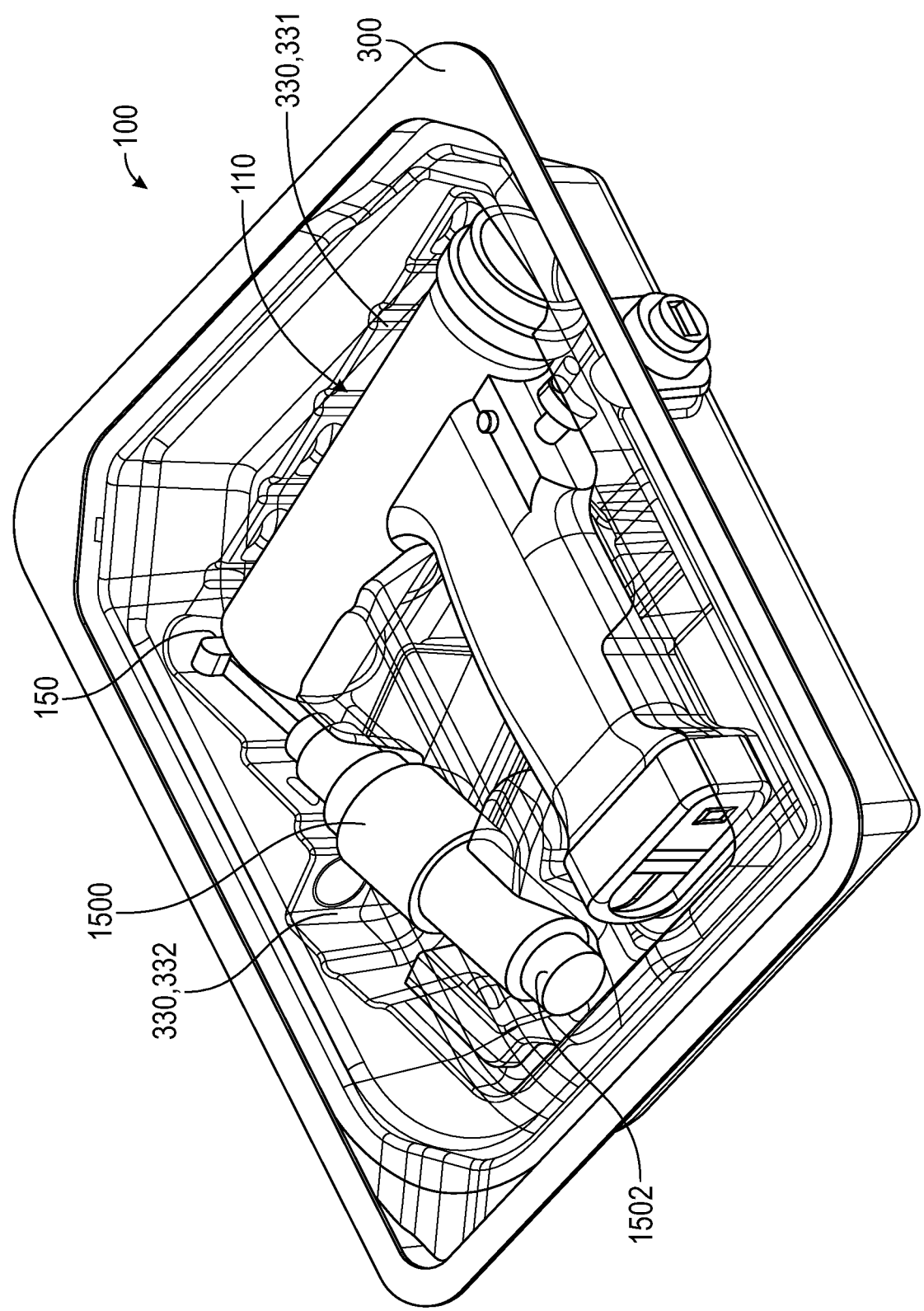
FIGS. 15A and 15B depict perspective views of a portable device and an attachment provided in a tray.
Figure 15B:
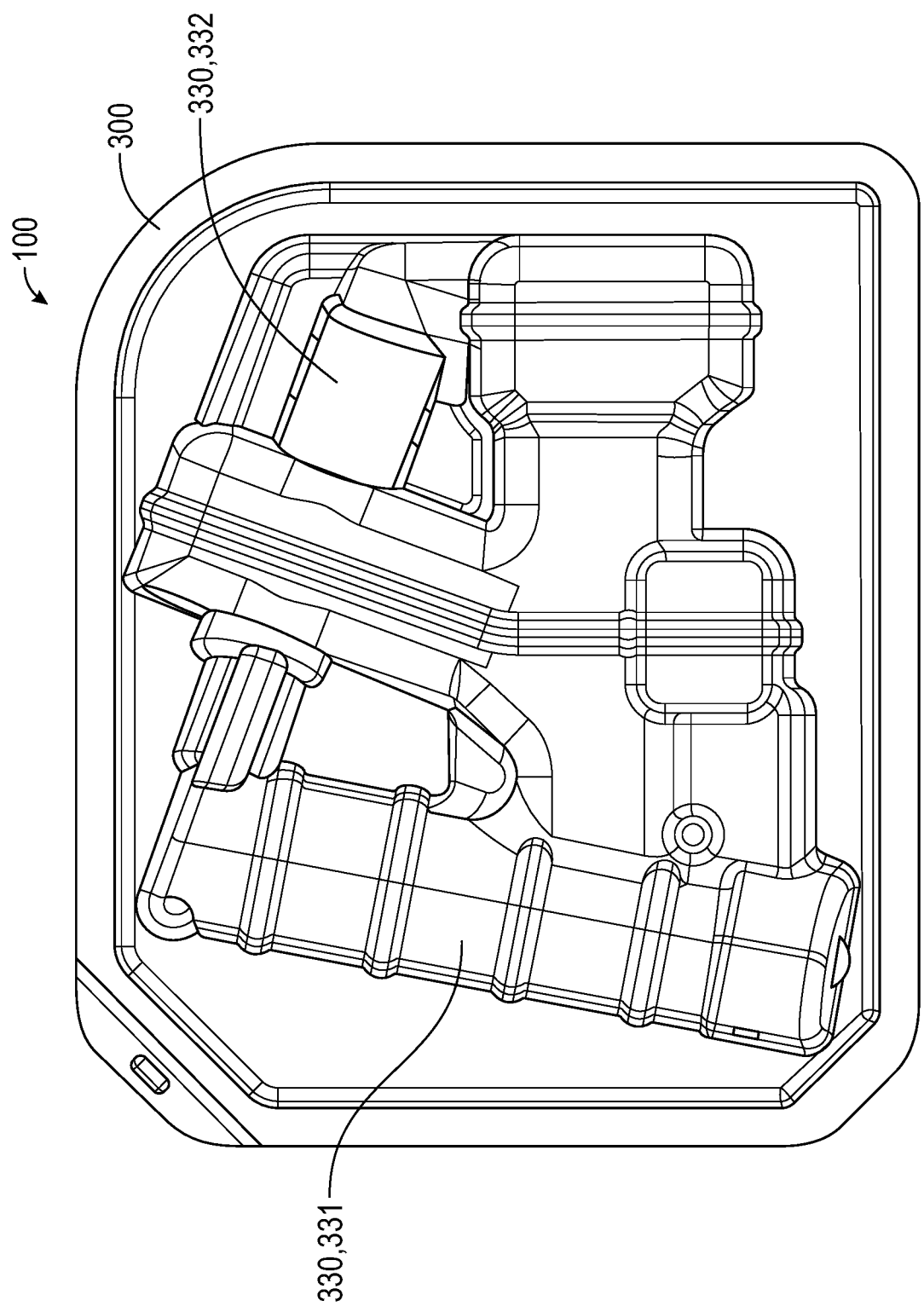

FIGS. 15A-15B illustrate an example of the portion 110 of the portable device 100 being secured within a first tray 300 along with one or more attachments 1500. For example, the portion 110 of the portable device 100 can include a driver which can be operable to provide power to and manipulate the attachments 1500. It should be appreciated that an attachment may be selected from a plurality of attachment types and operable to be inserted into attachment coupling 150. The attachments 1500 may include, but are not limited to, saw blades, wire/pin drivers, and/or drill chucks. The first tray 300 can include a first compartment 331 operable to securely receive the portion 110 of the portable device 100. The first tray 300 can also include a second compartment 332 operable to securely receive an attachment 1500. Accordingly, a kit can be provided that includes all the necessary tools (e.g., driver 110 and attachments 1500) to perform the procedure.

Figure 15C:
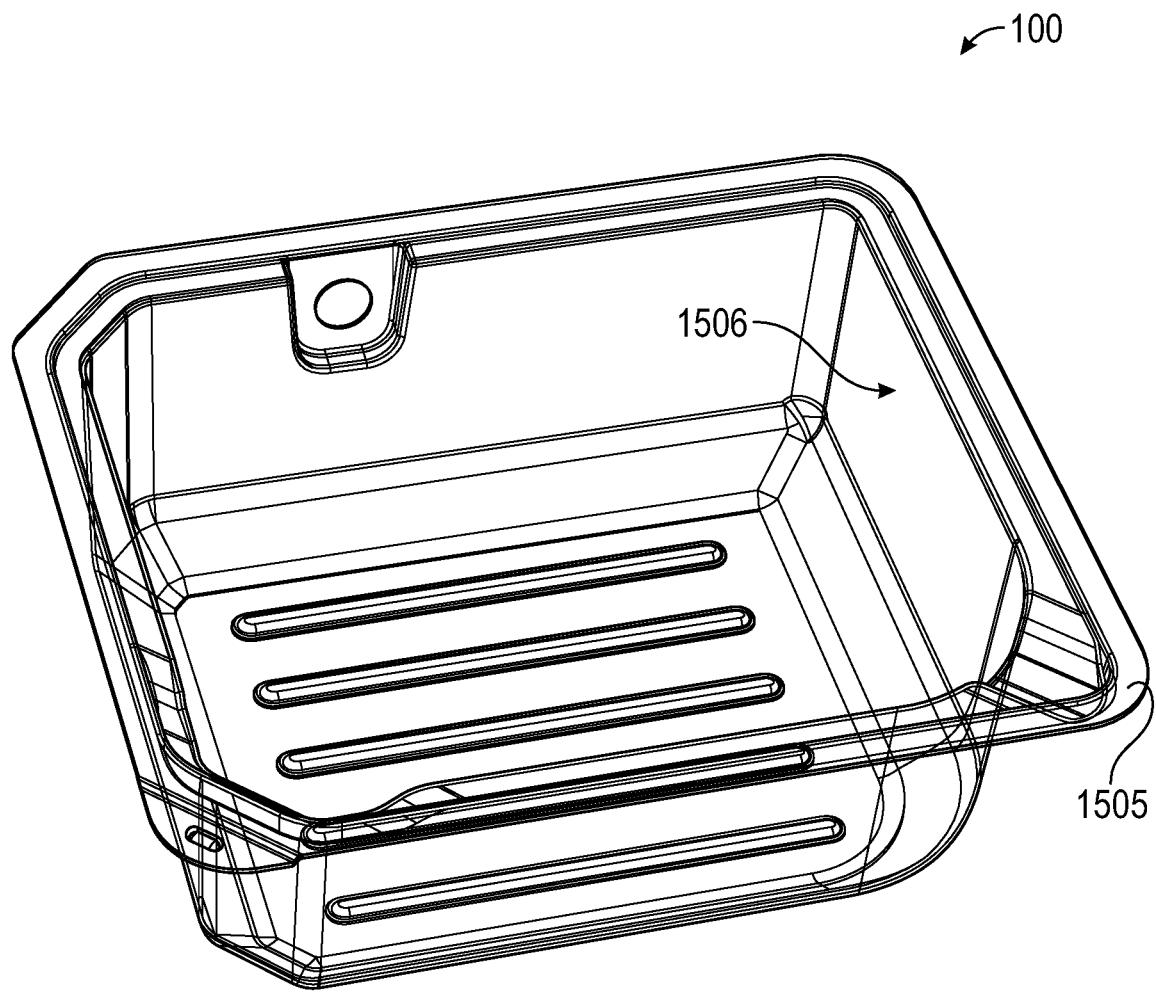
FIGS. 15C, 15D, and 15E depict a package operable to receive at least two trays to store a driver and a plurality of attachments.
Figure 15D:
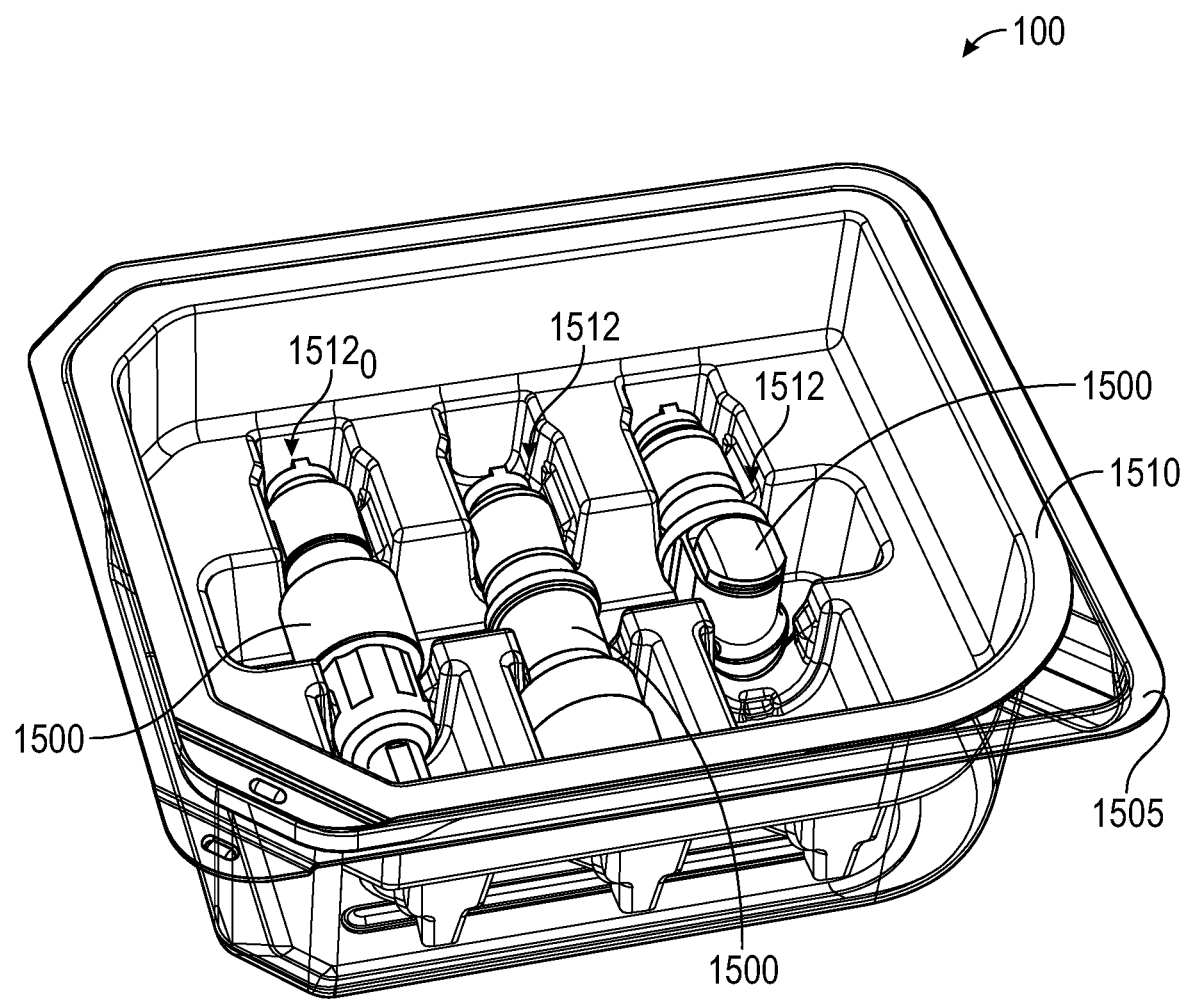
Figure 15E:
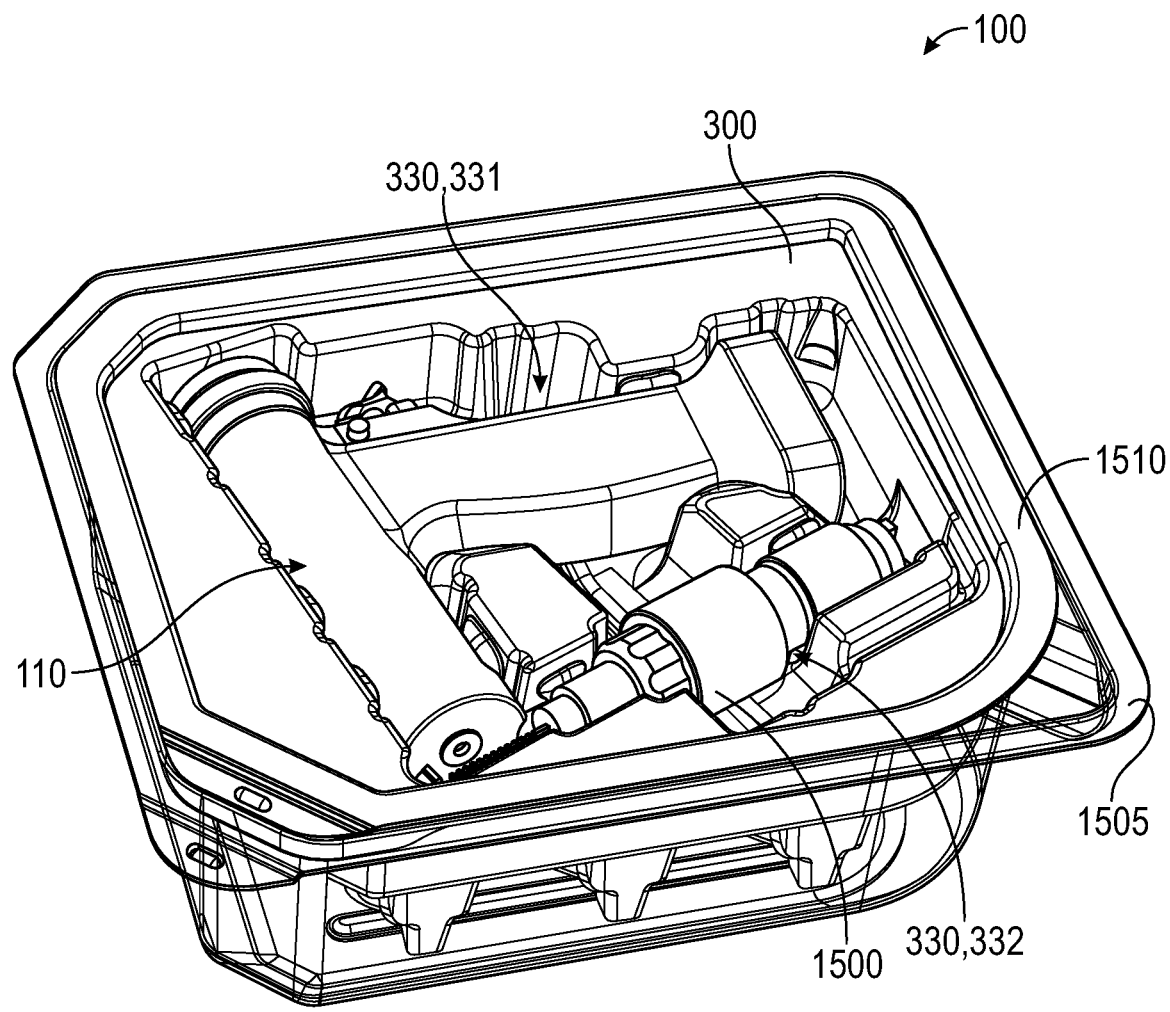

FIGS. 15C-15E illustrate an example of a package 1505 that is operable to receive one or more than one tray 1510, 300. A plurality of attachments 1500 can then be provided within the one package 1505 or kit. Accordingly, the kit can include all necessary attachments 1500 and the driver 110 to perform the procedure.

As illustrated in FIG. 15C, the package 1505 forms a receiving portion 1506 operable to receive one or more trays 300, 1510. As illustrated in FIG. 15D, an attachment tray 1510 is disposed within the receiving portion 1506 of the package 1505. The attachment tray 1510 forms a plurality of compartments 1512, each operable to receive an attachment 1500. As illustrated in FIG. 15D, the attachment tray 1510 forms three compartments 1512 such that the attachment tray 1510 is able to receive three attachments 1500. In other examples, the attachment tray 1510 can form one, two, or more than three compartments 1512, to correspond with the number of attachments 1500 needed or are able to fit within the attachment tray 1510.

FIG. 15E illustrates a first tray 300 being received by the attachment tray 1510 such that the first tray 300 is nested within the attachment tray 1510 which is nested within the package 1505. The first tray 300, as discussed above, can include a driver 110 received within a first compartment 331. In some examples, as illustrated in FIG. 15E, the first tray 300 can include one or more attachments 1500 received within a second (or more) compartment(s) 332.

While FIGS. 15C-15E illustrate the first tray 300 being received by and nested in the attachment tray 1510, in some examples, the attachment tray 1510 can be received by and nested in the first tray 300. Accordingly, the first tray 300 with the driver 110 is provided adjacent the bottom (e.g., further from the lid or cover) of the package 1505. This configuration can be beneficial as the first tray 300 with the driver 110 may be heavier than the attachment tray 1510, and it may be easier to charge the driver 110 in such a configuration.

While FIGS. 15C-15E illustrate a two-tiered kit with the attachment tray 1510 and the first tray 300 being received in the package 1505, in other examples, the kit can be three-tiered, four tiered, or more, depending on the number of attachments 1500 are needed for the procedure. Accordingly, the kit can provide all the tools needed for the procedure provided in a safe and sterile package.

Figure 16A:
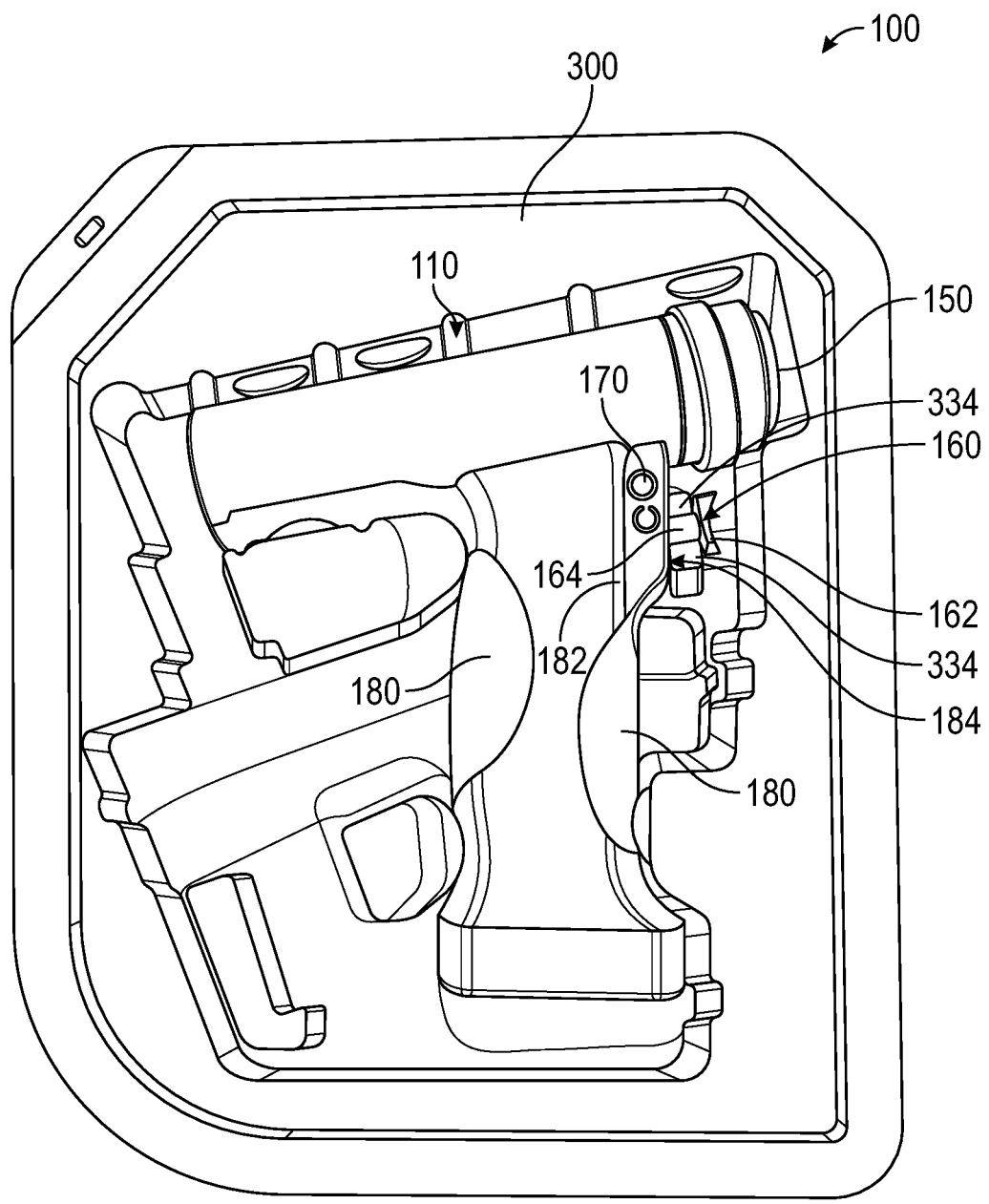
FIG. 16A depicts a top view of a tray forming a trigger guard for the driver.
Figure 16B:
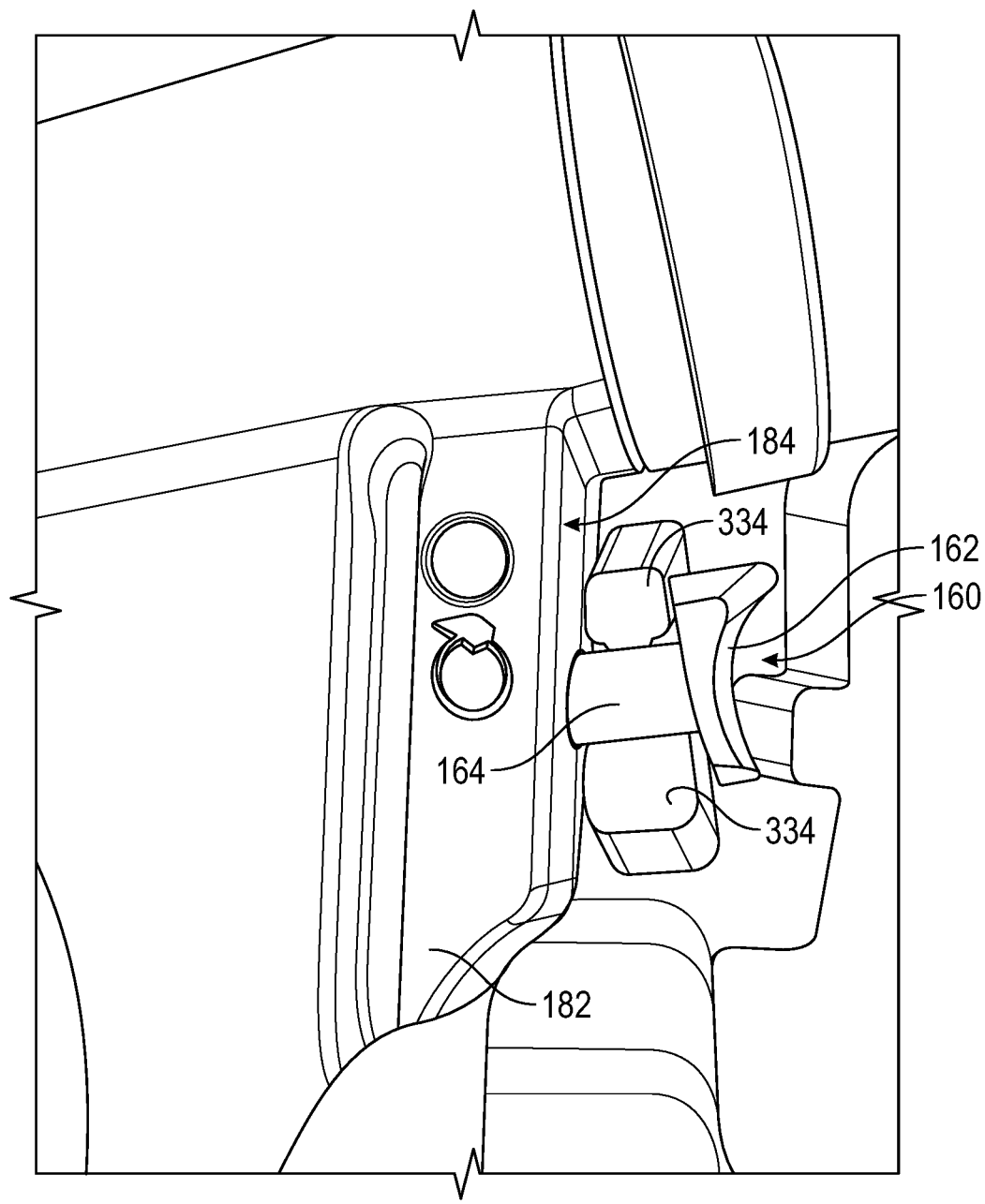
FIGS. 16B and 16C depict enlarged views of the trigger guard of FIG. 16A.
Figure 16C:
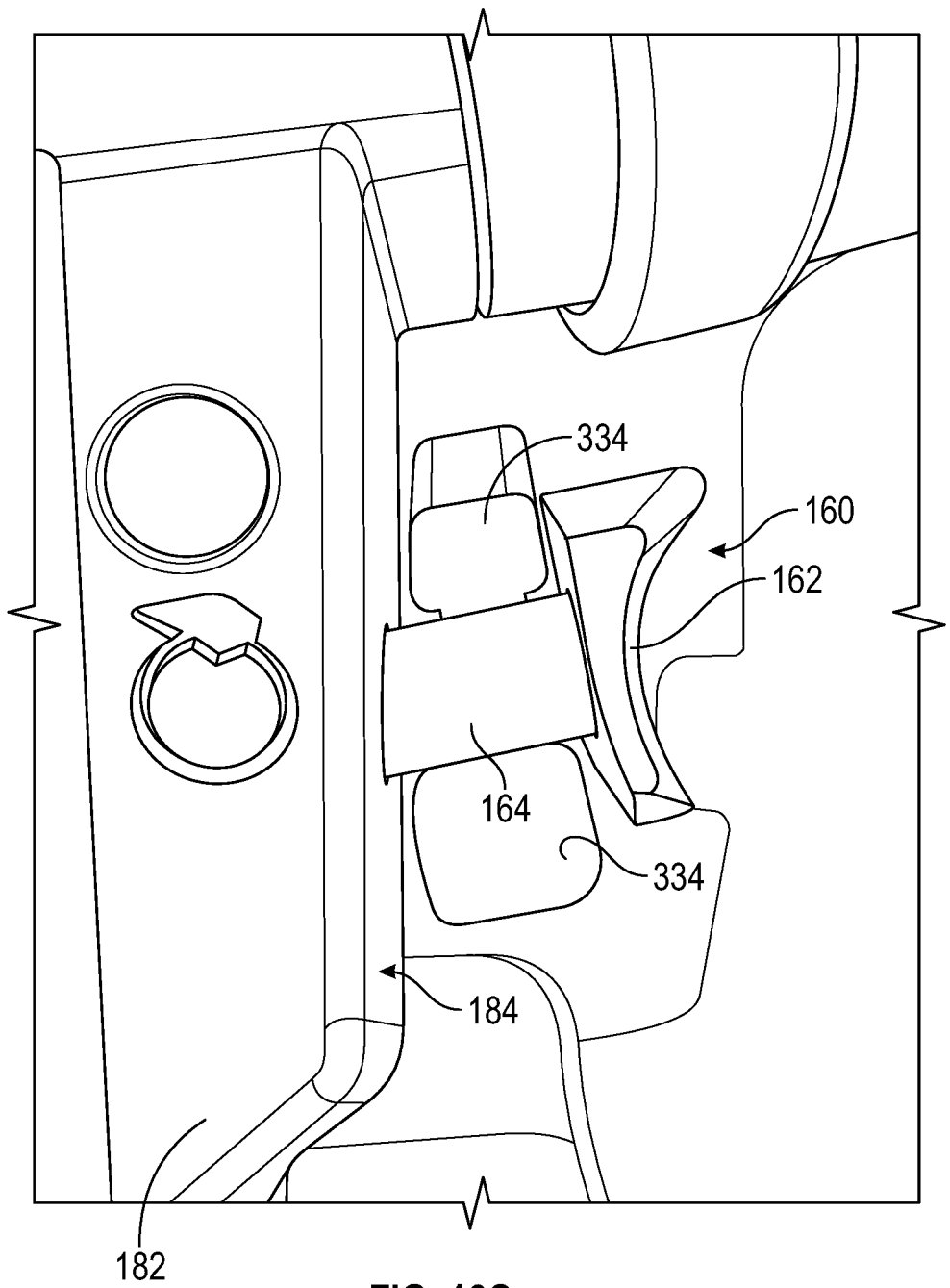

FIGS. 16A-16C illustrate a tray 300 operable to receive the driver 110 of the portable device 100. The driver 110 includes an attachment coupling 150 operable to couple with one or more attachments. The driver 110 can also include a handle 182 for a user to hold the driver 110 during operation of the driver 100. In some examples, the handle 182 can be disposed at an angle in relation to the attachment coupling 150. In some examples, the handle 182 can be in line with the attachment coupling 150. In some examples, as illustrated in FIG. 16A, the handle 182 can include one or more grips 180 to help the user hold onto the handle 182.

The driver 110 also includes a trigger 160. Trigger 160 may be provided to vary the speed of rotation of the interior of attachment coupling 150. It should be appreciated that trigger 160 may be provided to control the direction of rotation of the interior of attachment coupling 150 in a clockwise direction or in a counterclockwise direction without departing from the present disclosure. It should be appreciated that the driver 110 may provide a variable-speed trigger 160 and/or an instant-reverse trigger 160 in some embodiments of the present disclosure. As illustrated in FIGS. 16A-16C, the trigger 160 can extend from the handle 182. The trigger 160 can include an arm 164 extending from a surface 184 of the handle 182, and a finger rest 162 coupled to the arm 164. The trigger 160 can be actuated by enacting a force against the finger rest 162 so that the finger rest 162 moves towards the surface 184 of the handle 182. When the trigger 160 is actuated, the power supply of the driver 110 is activated to power the motor.

To prevent compression of the trigger 160, the tray 300 forms a trigger guard 334. In at least one example, the trigger guard 334 can be integrated with the tray 300 as one piece of material. In some examples, the trigger guard 334 can be coupled with the tray 300, for example by adhesive. The trigger guard 334 projects from and/or extends from the tray 330 such that the trigger guard 334 is disposed between the finger rest 162 and the surface 184 of the handle 182. In some examples, the trigger guard 334 can receive the arm 164 of the trigger 160 and abut against the inside of the finger rest 162 and abut against the surface 184 of the handle 182. Accordingly, if a force is enacted on the trigger 160 when the driver 110 is correctly received in the tray 300, the trigger guard 334 prevents the finger rest 162 from moving towards the surface 184 of the handle 182. In other words, the trigger guard 334 prevents compression of the trigger 160. Accordingly, the battery cannot be engaged while stored in the tray 300. This improves safety and sterility of the driver 110 while stored within the tray 300.

Any of the features discussed and illustrated in FIGS. 15A-16C can be implemented along with any of the features discussed and illustrated in FIGS. 1-14.

It should be appreciated that embodiments of the present disclosure may provide for usage in conflict zones or natural disasters, where charging equipment may not be possible. Further, usage may be provided in geographic locations that may not have access to an adequate power supply and/or sterile environment cannot fully charge medical equipment and instruments. However, usage in hospitals and other medical facilities may be improved insofar as devices containing tools necessary for medical procedures may be readily available off-the-shelf and for immediate use at a cost that has significant advantages over other reusable tool systems.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, and composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A kit for providing a sterile portable device and a plurality of attachments, the kit comprising:
   a portable device, the portable device being powered by at least one chargeable battery;
   a first tray operable to receive and secure the portable device;
   an attachment tray operable to receive and secure the plurality of attachments for the portable device;
   a package operable to receive the first tray and the attachment tray in a nested configuration and provide a sterile enclosure for the portable device and the plurality of attachments;
   a power supply operable to be electrically connected with the portable device such that the chargeable battery of the portable device is charged in the sterile environment.

2. The kit of claim 1, wherein the chargeable battery is arranged inside of the portable device.

3. The kit of claim 1, wherein the first tray is operable to receive and secure the portable device and one attachment.

4. The kit of claim 1, wherein the attachment tray is operable to receive and secure up to three attachments.

5. The kit of claim 1, wherein the first tray is operable to be nested within the attachment tray.

6. The kit of claim 1, wherein the attachment tray is operable to be nested within the first tray.

7. The kit of claim 1, wherein the attachments include saw blades, wire/pin drivers, and/or drill chucks.

8. The kit of claim 1, wherein the portable device is charged to a full capacity prior to opening the sterile environment.

9. The kit of claim 1, wherein the power supply supplies power to the chargeable battery corresponding with the portable device via a wireless charging station located external to the portable device having a transmitter operable to transmit power wirelessly to a receiver secured in the portable device.

10. The kit of claim 1, wherein the power supply supplies power to the chargeable battery corresponding with the portable device via wired connection.

11. The kit of claim 1, further comprising:
    a charging system to maintain the chargeable battery, the charging system including a chip or a PCB operable to control a charge current to the chargeable battery.

12. The kit of claim 11, further comprising:
    a fuse operable to disconnect the chargeable batteries from the power supply when a fuse triggering event occurs.

* * * * *